United States Patent
Johnson

(10) Patent No.: US 8,284,068 B2
(45) Date of Patent: Oct. 9, 2012

(54) ACTIVITY MONITOR TO ALLEVIATE CONTROLLED SUBSTANCE ABUSE

(76) Inventor: Sam Johnson, Las Vegas, NV (US)

( * ) Notice: Subject to any disclaimer, the term of this patent is extended or adjusted under 35 U.S.C. 154(b) by 0 days.

(21) Appl. No.: 13/072,971

(22) Filed: Mar. 28, 2011

(65) Prior Publication Data

US 2011/0169635 A1    Jul. 14, 2011

Related U.S. Application Data

(63) Continuation-in-part of application No. 12/503,065, filed on Jul. 14, 2009.

(51) Int. Cl.
*G08B 21/00* (2006.01)

(52) U.S. Cl. .............. 340/669; 340/568.1; 340/571

(58) Field of Classification Search ............ 340/669, 340/568.1, 693.5, 532, 686.1, 681, 691.1, 340/691.6, 309.16, 309.4, 309.7, 309.8, 571; 600/300; 368/244, 277; 705/2, 3
See application file for complete search history.

(56) References Cited

U.S. PATENT DOCUMENTS

| | | | | |
|---|---|---|---|---|
| 6,529,446 B1 * | 3/2003 | de la Huerga | ............ | 368/10 |
| 7,553,235 B2 * | 6/2009 | Walker et al. | ............ | 463/43 |
| 7,821,404 B2 * | 10/2010 | Walker et al. | ............ | 340/573.1 |
| 7,896,192 B2 * | 3/2011 | Conley et al. | ............ | 221/15 |
| 7,944,342 B2 * | 5/2011 | Sekura | ............ | 340/309.4 |
| 7,993,055 B2 * | 8/2011 | Nurse et al. | ............ | 368/277 |
| 8,069,056 B2 * | 11/2011 | Walker et al. | ............ | 705/2 |

* cited by examiner

*Primary Examiner* — Toan N Pham
(74) *Attorney, Agent, or Firm* — Smith Risley Tempel Santos LLC; Gregory Scott Smith

(57) ABSTRACT

An activity monitor which can be pre-programmed at the factory, the doctors office or the pharmacist, or that can be programmed by the user. The activity monitor is affixed to a medicine bottle or container and activity associated with the bottle or container, such as movement, opening, volume changes, etc. are monitored in view to the schedule. The activity monitor records and allows for the analysis of the recorded data to determine is there is a likelihood of substance abuse.

4 Claims, 13 Drawing Sheets

ACTIVITY MONITOR TO ALLEVIATE CONTROLLED SUBSTANCE ABUSE

CROSS-REFERENCE TO RELATED APPLICATIONS

This is a non-provisional application filed in the United States Patent Office under 37 CFR 1.53(b) and 35 USC. 111 as a continuation-in-part of, and claiming priority to, the United States Non-provisional application that was filed on Jul. 14, 2009, assigned Ser. No. 12/503,065 and bearing the title of "MOTION OR OPENING DECTOR".

BACKGROUND OF THE INVENTION

One of the cruelest jokes we have ever played on ourselves is the naming of the memory medicine Ginkgo Biloba. Not a smart marketing strategy either. Nonetheless, the product tends to sell and a reason for the sales may simply be that most of us are plagued and frustrated by memory failures. These symptoms manifest itself in trying to remember a person's name, an item that our spouse asked us to pick up at the grocery store, or even simply the reason that we got up off of the couch, walked all the way into another room in the house and then stood there wondering why. Most of these situations can be comically laughed off; however, there are situations where memory failures can be quite problematic or even catastrophic.

A perfect example of a situation in which the adverse affect of memory lapses can be realized is in the taking or administering of medication. Depending on the medication and the individual, failure to take medication can result in severe harm. In view of this, one can appreciate that it can be very important to remember to take or administer medication, and to do so in a timely manner. Thus, what is needed in the art is a mechanism that can remind or notify an individual that he or she must take or administer medication, and even when the medication must be taken or administered.

Another example of a situation in which the adverse affect of memory lapses can be realized is in remembering that you have already received or administered a medication. Such memory lapses can result in an overdose of a medication. In view of this, one can appreciate that it would be advantageous to have a device that keeps track of taken and/or administered dosages, notifies or alerts an individual attempting to take or administer an overdose and/or takes measures to help prevent overdosing.

Yet again, with disregard to memory elements, there is a high number of individuals that engage in taking prescribed medications either legally or illegally. Most medications that are prescribed to individuals, as well as animals, are provided in containers, such as pill bottles, bottles of serum, or pill pouches etc. The packaging for medication can conveniently operate as a dosage reminder/control gateway in that the person taking or administering the medication at a minimum, must approach the packaging to obtain the dosage. In view of this characteristic, there is a need in the art for a dosage reminder or overdose preventer mechanism that can be attached to, adhered to or otherwise be associated with the packaging.

Related to these needs in the art there are additional needs in the art with respect to determining if a container in general has been opened, moved, tampered with, etc., as well as providing historical data about such activity with the container and providing alerts regarding such activity. These needs in the art can arise in a variety of settings, and a few examples include detecting movement or opening of a liquor bottle, detecting opening of a liquor or gun cabinet, detect movement of a moisture testing apparatus, etc.

Therefore, there is a need in the art for a device that can be used to detect when a container, such as a medicine package or otherwise, has been moved, opened or otherwise tampered with, collecting and storing information about such activity, and reporting to or alerting a person or system of such activity.

Most individuals take medicines only for the reasons their doctors prescribe them and generally at the proper times and in the proper dosages. But an estimated 20 percent of people in the United States have used prescription drugs for nonmedical reasons. This type of usage is referred to as prescription drug abuse. Prescription drug abuse means taking a prescription medication that is not prescribed for you, or taking it for reasons or in dosages other than as prescribed. Abuse of prescription drugs can produce serious health effects, including addiction. Commonly abused classes of prescription medications include opiods (for pain), central nervous system depressants (for anxiety and sleep disorders), and stimulants (for ADHD and narcolepsy). Opioids include hydrocodone (Vicodin®), oxycodone (OxyContin®), propoxyphene (Darvon®), hydromorphone (Dilaudid®), meperidine (Demerol®), and diphenoxylate (Lomotil®). Central nervous system depressants include barbiturates such as pentobarbital sodium (Nembutal®), and benzodiazepines such as diazepam (Valium®) and alprazolam (Xanax®). Stimulants include dextroamphetamine (Dexedrine®), methylphenidate (Ritalin® and Concerta®), and amphetamines (Adderall®).

Prescription drug abuse is a serious and growing problem. Experts differ on the reasons as to why prescription drug abuse is increasing. But, there are likely multiple factors that are resulting in this trend.

One such factor may be the misperceptions about the safety of taking these prescription drugs. Because these medications are prescribed by doctors, many assume that they are safe to take under any circumstances. This is not the case: prescription drugs act directly or indirectly on the same brain systems affected by illicit drugs; thus their abuse carries substantial addiction liability and can lead to a variety of other adverse health effects.

Another factor may be due to increasing environmental availability. Between 1991 and 2009, prescriptions for stimulants increased from 5 million to nearly 40 million, an 8-fold increase, and opioid analgesics increased from about 45 million to approximately 180 million, more than a 4-fold increase. Doctors are prescribing more drugs for more health problems than ever before. Online pharmacies make it easy to get prescription drugs without a prescription, even for youngsters.

Further, there are varied motivations for the abuse of these prescription drugs. Underlying reasons include: to get high; to counter anxiety, pain, or sleep problems; or to enhance cognition (although they may, in fact, impair certain types of cognitive performance).

According to the NIDA website, in 2008, 15.2 million Americans age 12 and older had taken a prescription pain reliever, tranquilizer, stimulant, or sedative for nonmedical purposes at least once in the year prior to being surveyed. Source: National Survey on Drug Use and Health (Substance Abuse and Mental Health Administration Web Site). The NIDA-funded 2008 Monitoring the Future Study showed that 2.9% of 8th graders, 6.7% of 10th graders, and 9.7% of 12th graders had abused Vicodin and 2.1% of 8th graders, 3.6% of 10th graders, and 4.7% of 12th graders had abused OxyContin for nonmedical purposes at least once in the year prior to being surveyed. Source: Monitoring the Future (University of Michigan Web Site)

In 2009, approximately 7.0 million persons reported past month non-medical use of psychotherapeutic drugs (2.8 percent of the U.S. population). This class of drugs is broadly described as those targeting the central nervous system, including drugs used to treat psychiatric disorders (NSDUH, 2009).

Among adolescents, prescription and over-the-counter medications account for most of the frequently abused drugs, following marijuana (excluding tobacco and alcohol). Nearly 1 in 12 high school seniors reported nonmedical use of Vicodin; 1 in 20 reported abuse of OxyContin. Overall, 1 in 5 teenagers abuse prescription drugs. When asked how prescription narcotics were obtained for nonmedical use, 59% of 12th graders said they were given to them by a friend or relative. The number obtaining them over the internet was negligible.

Thus, there is a need in the art for a solution that can help detect prescription drug abuse and provide information to experts that can be used to identify abuse, report abuse and control abuse.

Today, it is common place to see employers requiring a substance abuse screening as a requirement for employment. Some states, such as Kentucky for example, are taking action with regards to individuals receiving public assistance. Representative Lonnie Napier from Lancaster has filed a bill for the 2011 session that would require drug and substance screening for any adults in Kentucky receiving public assistance, including food stamps and state medical assistance. Napier says it is essential to require anyone receiving government assistance to submit to testing. The random testing through the Cabinet for Health and Family Services would be a prerequisite to an individual being declared eligible for public assistance, but it would allow for exceptions if the individual has a prescription for a controlled substance.

Thus, there is a need in the art for a system, device or method that can be used to provide information to employers and government officials regarding an individual's use of prescription drugs.

BRIEF SUMMARY OF THE INVENTION

In a broad sense, the disclosure presents an activity monitor that can be attached, affixed or integrated into a variety of devices, such as to the existing packaging of consumer goods that otherwise would not have such capability, and provide monitoring, alerting and/or reporting activity associated with the device. In one embodiment, the activity monitor operates as a medicine reminder. This embodiment includes a schedule which can be pre-programmed at the factory, the doctor's office or the pharmacist, can be programmed by the user, or simply be programmed automatically by learning the behavior of the user. The activity monitor is then affixed to the medicine bottle and activity associated with the bottle, such as movement, opening, volume changes, etc. are monitored in view to the schedule. If the schedule indicates that a dose of medicine should be taken at a particular time, but the monitored activity does not determine that the medicine has been taken, an alert signal will be issued to alert the user that it is time to take the medicine. In addition, if the monitored activity indicates that the medicine bottle has been opened prior to a scheduled time, then a tamper alert can be triggered.

In another embodiment, the activity monitor operates only as a tamper detector. In this embodiment, the activity monitor is attached to a device or container and then started. Any movement or activity associated with the device or container is analyzed and/or recorded and may result in triggering a tamper alarm. In some embodiments, the tamper detector may define windows of time during which activity is permitted to occur and during which activity is not permitted to occur. Activity occurring during a permitted window will not trigger a tamper alarm.

In one embodiment the activity monitor can be used by insurance companies to help alleviate the abuse of controlled substances. In such an embodiment, the insurer (which may be individuals or a processing system operating and operated on behalf of the insurer) may offer a discount for the controlled substance if the insured individual agrees to receive the prescription in an activity monitored container or to employ the use of an activity monitor. For such insured individuals, the controlled substance, administered in accordance with the prescription requirements, is provided to the insured along with an activity monitor. The substance may be within a container that includes an integral activity monitor or, along with an activity monitor that can be attached or coupled to a container housing the substance. The activity monitor then records activity events related to the dispensing of the controlled substance, such as container openings, closings, timing of events, removal of contents, etc. The insurer then receives the recorded activity events and then conducts an analysis of the event data. If the event data indicates that there may have been activity that is suspicious of abuse, then the insurer can take remedial actions, such as raising the premium for the insured, refusing further payment for subscriptions, requiring the insured to seek professional counseling, etc.

In some embodiments, the container and activity monitor may include a lock-out mechanism. In such embodiments, the controlled substance is placed within the container for shipment and, when the container is closed, the lock-out mechanism is triggered to force the container into a lock-out state in which the contents cannot be accessed. The insurer then receives a request to reset the lock-out mechanism from an insured individual that has received the activity monitored container with the controlled substance. In response to the request, possibly after the insured is authenticated and verified, the insurer resets the lock-out mechanism such that the insured individual can access the controlled substance.

Another embodiment includes method for detecting suspected abuse of controlled substances. This embodiment operates by a pharmacy receiving a prescription for a controlled substance. The pharmacy provides the filled prescription to an individual in an activity monitored container. The activity monitored container monitors activity of the activity monitored container related to opening of the container and removal of substance and records activity events and associated time stamps into a memory element. After a period of time, such as a 30 day prescription period or the like, the pharmacy receives the activity monitored container from the individual. The pharmacy then accesses data stored within the activity monitor and analyzes the retrieved recorded activity. This activity can then be reported to a third party such as an insurance provider of the individual, the guardian of the individual, law enforcement authorities, the individual's doctor, etc.

In addition or in lieu of such reporting, the pharmacy may deny the fulfillment of a refill request if the recorded activity indicates suspicious behavior or provide a refill if the activity indicates normal behavior.

In another scenario, a physician may be required to issue the monitoring device with all or certain prescriptions or for certain patients. When the doctor receives the activity monitor from the patient, he or she can determine if there has been any misuse. If any misuse is detected, the doctor may be required to conduct additional screening of the patient before he can write another prescription or refill. Advantageously, this aspect puts the physician in the loop as a key element in helping to curtail this problem. Further, such a system can limit the ability of physicians to abuse the system as they will not be able to freely write prescriptions without some level of accountability.

These and many other embodiments, as well as various features, aspects and functions of the various embodiments are more fully presented below.

DETAILED DESCRIPTION OF THE DISCLOSURE

Figure 1A:
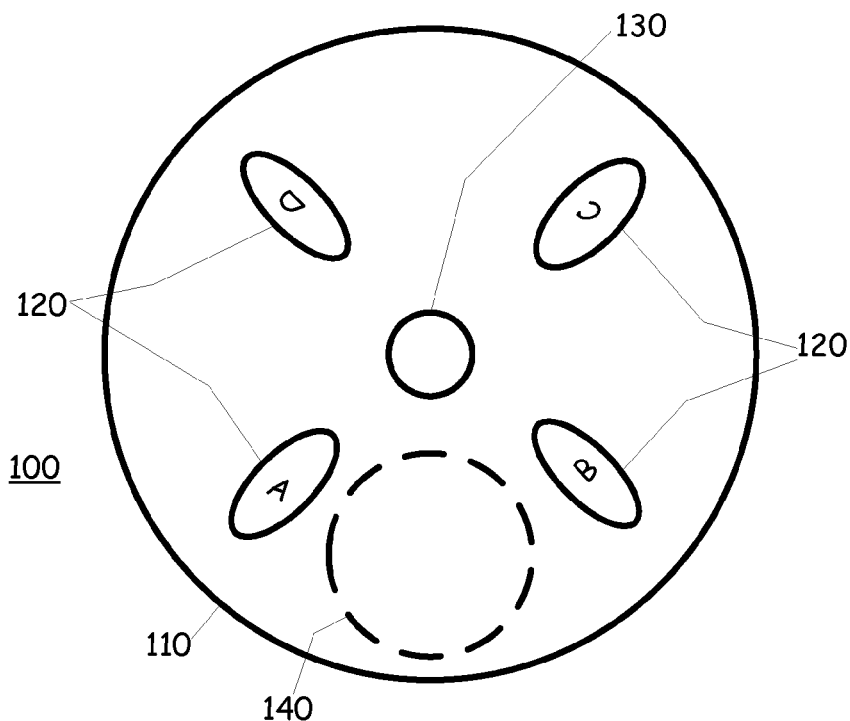
FIG. 1 is a conceptual depiction of one embodiment of the activity monitor with FIG. 1A illustrating a top view and FIG. 1B illustrating a side view.

The present disclosure, as well as features and aspects thereof, is directed towards an activity monitor device, apparatus and/or method that monitors activity associated with a container. More specifically, one embodiment of the activity monitor utilizes an accelerometer to detect movement of the container and based on the movement, type of movement, and timing of the movement, can heuristically determine the type of activity associated with the movement. In another embodiment of the activity monitor, an alert or alarm component may be used to signal or indicate that the container has been moved or opened. In yet another embodiment of the activity monitor, signals may be provided based on a timing component to alert a user or device that the container should be accessed. In other embodiments, devices or mechanisms may be used to detect if a container is opened or if a top or cap has been removed from a container (i.e., a pill bottle cap). One such method to detect if the cap was actually opened is first by using a motion sensor as previously described, then a piezo signal is sent to the inside of the bottle. The time of sending the signal is monitored as well as the time that the signal is returned, if at all. If the signal is returned, it is concluded that the cap or top of the container is closed. However, when the cap is actually opened, the piezo signal is not returned thus the cap is identified as being open. This technique can be used in conjunction with or alternative to an accelerometer. Similarly, another solution may be as simple as having a circuit/sensor between the container (bottle) and the to (cap). In this embodiment, when the circuit is broken the cap is determined to have been removed. It will be appreciated that the activity monitor presented in this disclosure may be used in a variety of settings and environments, and may be used for a variety of purposes. Specific examples are illustrated and described within the disclosure to provide a general, overall and specific understanding of the various aspects, functions, operations and capabilities of the activity monitor but, such specific examples are provided as non-limiting examples.

One specific example in which an embodiment of the activity monitor may be utilized in within the context of a medicine bottle is activity monitor. In this example, the activity monitor can operate as a medicine reminder to: (a) signal a user that it is time to take or administer the specific prescription medication, vitamin, over the counter medication, herb etc. (collectively referred to as medicine) that is stored in the bottle, (b) alert or indicate to the user that the medicine has already been taken and that no additional dosages are due at the present time, (c) assist the user in finding the medicine bottle, and/or (d) alert or indicate to the user, a doctor, a pharmacists, court, probation officer, 12-step recovery sponsor, etc. that someone has moved or opened the bottle at an inappropriate time.

Further elaborating on activity monitor for a medicine bottle, one embodiment may include a small device that can be attached to the top or cap of the medicine bottle. When the cap on the monitored medicine bottle has not been opened at a scheduled time the activity monitor enters a "reminder alert" state indicating that the content in the medicine bottle has not been take at its scheduled time or within a scheduled window of time. Additionally, the activity monitor can alert the user if the container has been improperly tampered with by someone that the content is not intended for (e.g. teenage kids in the household) and signals this to the user by entering a "tamper alert" state. Further, the activity monitor can provide a higher-level of service by recording and providing or sending the time and the dosage taken of a medication to a central system. This information, along with other information that can be collected by other health monitoring devices (such as that manufactured by Dexcom) attached to the body can be pertinent information to provide a more real-time evaluation of the performance and impact that a medication is having on a patient, rather than having to make a 2 month follow-up visit.

Turning now to the figures in which several embodiments of the activity monitor are presented and common elements are represented with common labels, the various elements of the embodiments are presented in more detail.

Figure 1B:
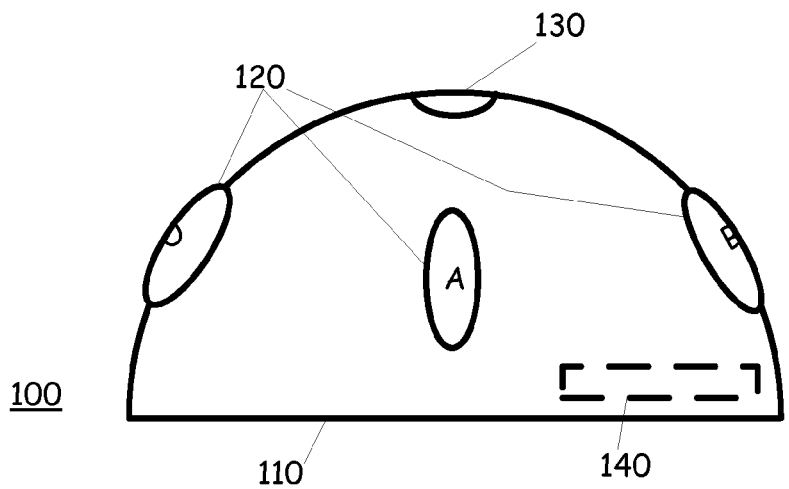

FIG. 1 is a conceptual depiction of one embodiment of the activity monitor with FIG. 1A illustrating a top view and FIG. 1B illustrating a side view. The activity monitor 100 includes a case 110. Positioned on the top of the case 110 are four buttons 120 (A, B, C and D) and an alert element 130. The activity monitor 100 includes electronic circuitry and/or software, including an accelerometer and a battery power source 140 (shown in dotted lines as they are embedded within the device). The electronic circuitry interfaces to the four buttons or actuators 120, the accelerometer and the alert element 130.

Figure 2:
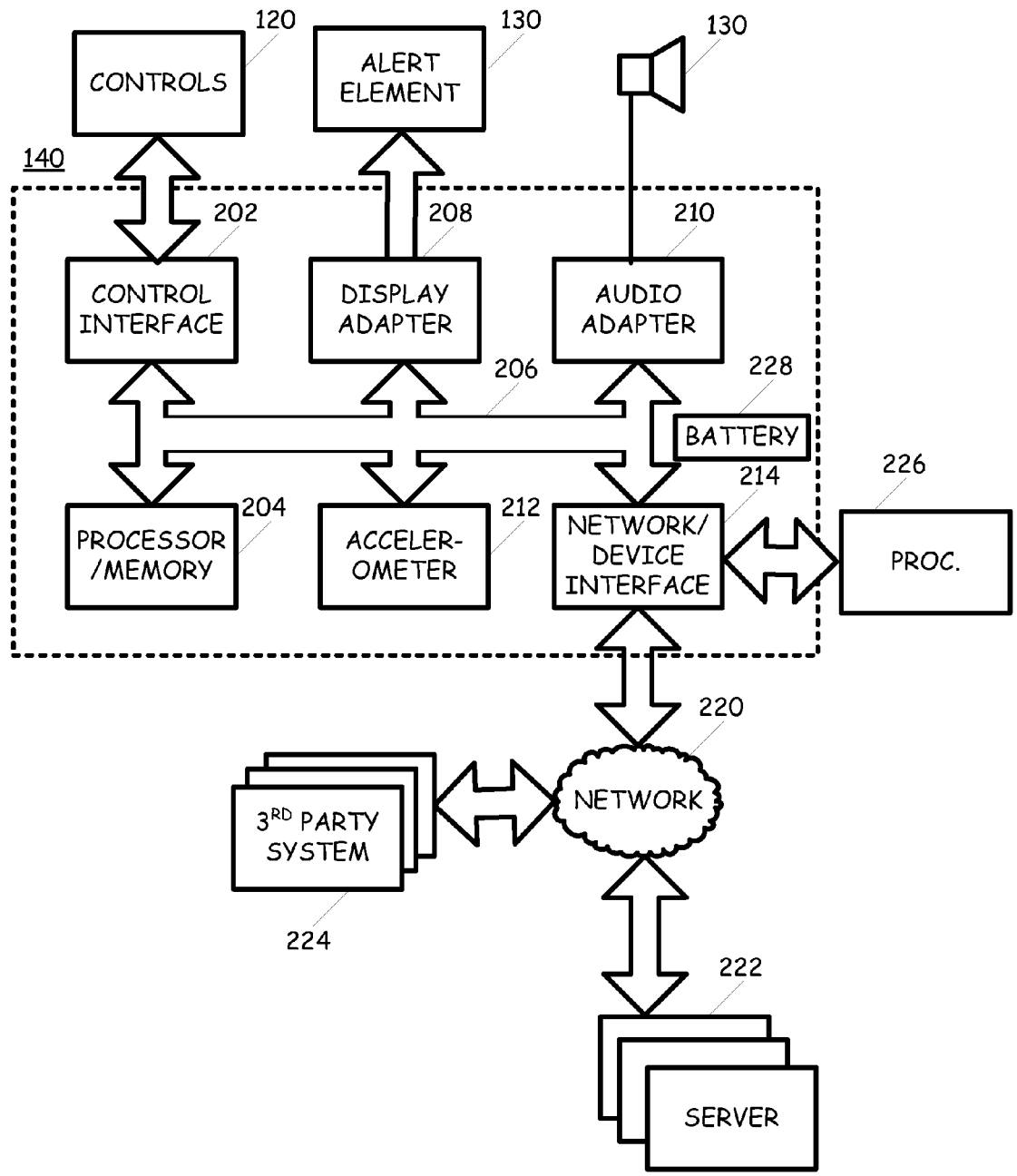
FIG. 2 is a functional block diagram of the components of an exemplary embodiment of the electronic circuitry 140.

FIG. 2 is a functional block diagram of the components of an exemplary embodiment of the electronic circuitry 140. It will be appreciated that not all of the components illustrated in FIG. 2 are required in all embodiments of the activity monitor but, each of the components are presented and described in conjunction with FIG. 2 to provide a complete and overall understanding of the components. The electronic circuitry can include a general computing platform 140 illustrated as including a processor/memory device 204 that may be integrated with each other or, communicatively connected over a bus or similar interface 206. The processor 204 can be a variety of processor types including microprocessors, micro-controllers, programmable arrays, custom IC's etc. and may also include single or multiple processors with or without accelerators or the like. The memory element of 204 may include a variety of structures, including but not limited to RAM, ROM, magnetic media, optical media, bubble memory, FLASH memory, EPROM, EEPROM, etc. The processor, or other components may also provide components such as a real-time clock, analog to digital convertors, digital to analog convertors, etc. The processor 204 also interfaces to a variety of elements including a control interface 202, a display adapter 208, audio adapter 210, an accelerometer 212 and network/device interface 214. The control interface 202 provides an interface to external controls 120, such as sensor, actuators or the like. The display adapter 208 can be used to drive a variety of alert elements 130, such as display devices including an LED display, LCD display, one or more LEDs or other display devices. The audio adapter 210 interfaces to and drives another alert element 130', such as a speaker or speaker system, buzzer, bell, etc. The network/device interface 214 may interface to a variety of devices (not shown) such as a keyboard, a mouse, a pin pad, and audio activate device, a PS3 or other game controller, as well as a variety of the many other available input and output devices or, another computer or processing device 226. The network/device interface 214 can also be used to interface the computing platform 140 to other devices through a network 220. The network may be a local network, a wide area network, wireless network, a global network such as the Internet, or any of a variety of other configurations including hybrids, etc. The network/device interface 214 may be a wired interface or a wireless interface. The computing platform 140 is shown as interfacing to a server 222 and a third party system 224 through the network 220. A battery or power source 228 provides power for the computing platform 140.

In some embodiments the activity monitor may interact with other activity monitors or devices through a zigbee type network architecture. In such an embodiment, the activity monitors can gain intelligence by detecting, receiving and learning other activities or other drugs, medications or substances that were also taken, and at what time (e.g. other vitamins with certain food, this drug with this food, etc.) and then interface with the other devices to provide recommendations, warnings or instructions about any potential overdoses, drug interactions, etc.

Figure 3:
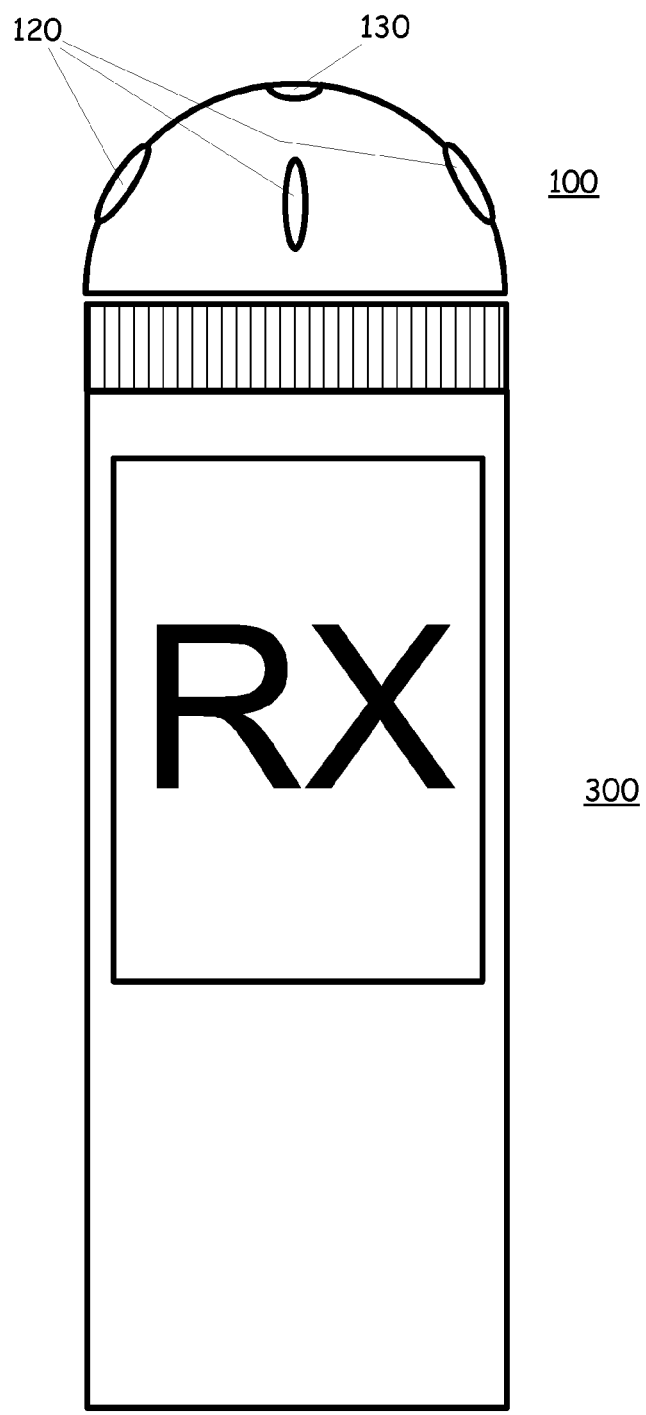
FIG. 3 is a conceptual diagram illustrating one environment suitable for various embodiments of the activity monitor.

FIG. 3 is a conceptual diagram illustrating one environment suitable for various embodiments of the activity monitor. In this embodiment, the activity monitor 100 is shown as being attached or affixed to a medicine bottle 300 containing medicine to be administered. The activity monitor 100 is attached to the top cap of the medicine bottle using any of a variety of techniques, including gluing, adhesive tape, snaps or similar rigid connectors, a screw, tabs, etc. One embodiment of the activity monitor 100 includes a pre-attached adhesive tape component with a protective cover. In this embodiment, to attach the activity monitor 100 to the medicine bottle 300, the adhesive protector is simply removed and the tacky surface is pressed against the medicine bottle top or cap. From this point, the activity monitor 100 is then ready to be programmed or activate to schedule and/or monitor use of the content in the container.

Figure 4:
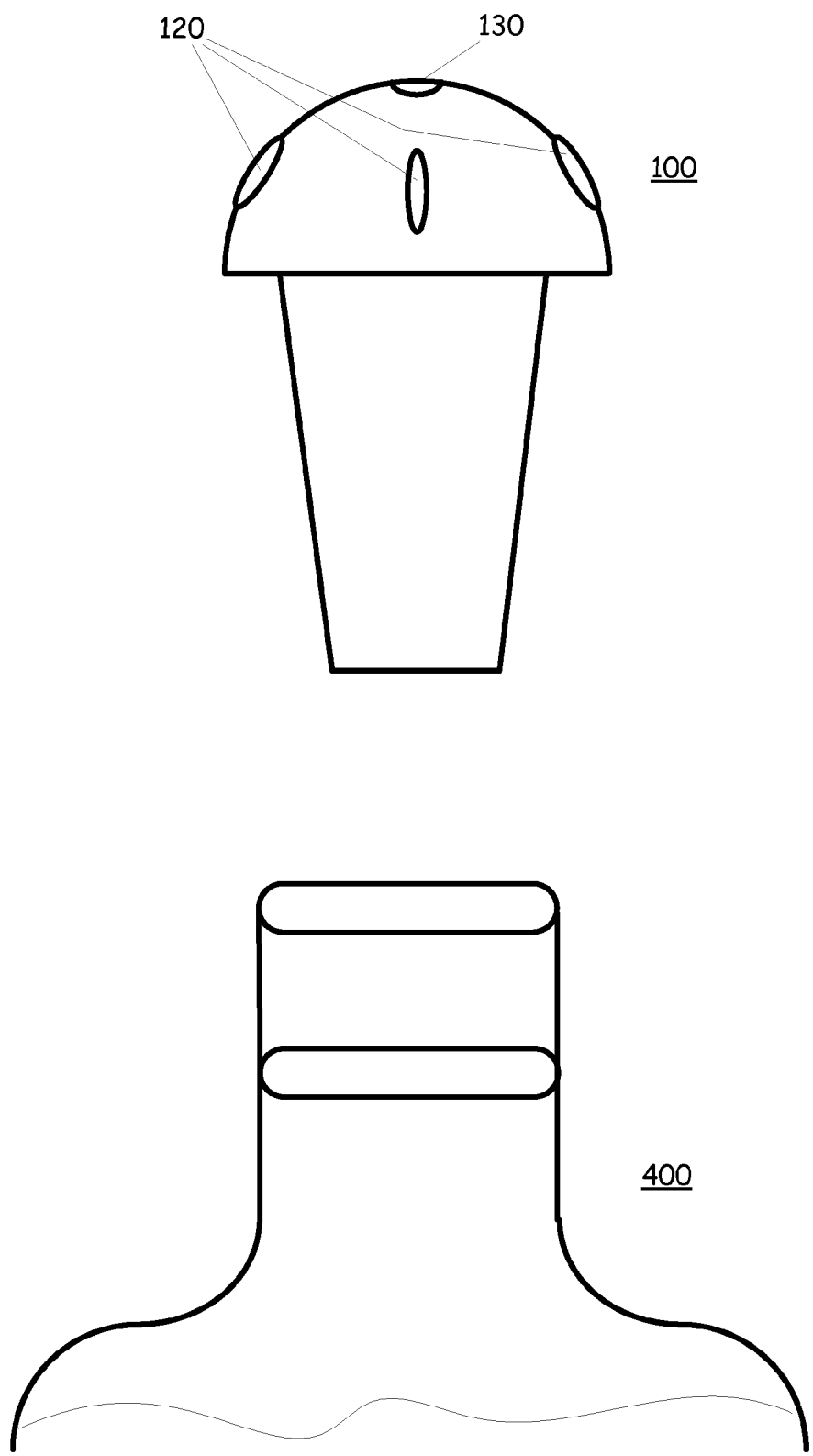
FIG. 4 is a conceptual diagram illustrating another environment suitable for various embodiments of the activity monitor.

FIG. 4 is a conceptual diagram illustrating another environment suitable for various embodiments of the activity monitor. In this embodiment, the activity monitor 100 is shown as being attached, affixed or integrated into a cork or stopper for a bottle, such as a liquor bottle, medicine bottle or any other type bottle 400. In this embodiment, the activity monitor 100 can come with the bottle 400 or sold separately and use after the bottle is initially opened. Once the stopper with the activity monitor 100 is inserted into the bottle, the bottle can then be monitored.

Figure 5:
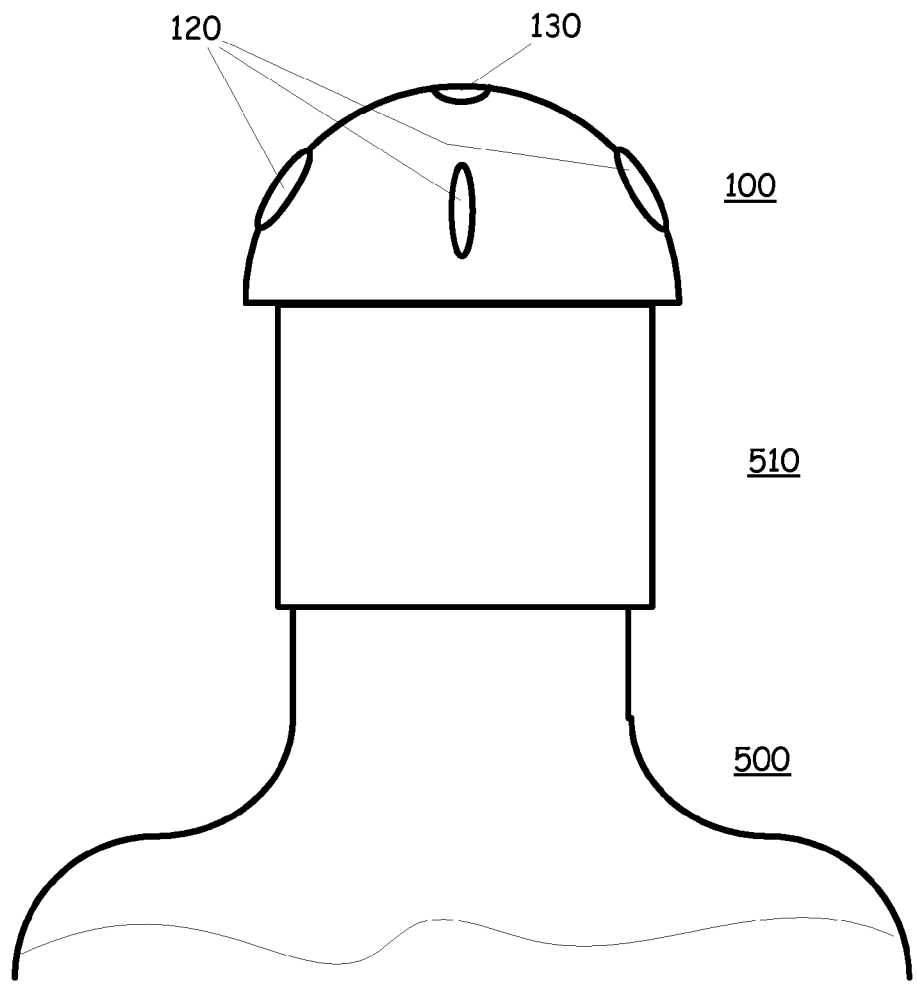
FIG. 5 is a conceptual diagram illustrating another environment suitable for various embodiments of the activity monitor.

FIG. 5 is a conceptual diagram illustrating another environment suitable for various embodiments of the activity monitor. In this embodiment, the activity monitor 100 is shown as being attached, affixed or integrated into a screw-on bottle cap 510, such as a liquor bottle, medicine bottle or any other type bottle 500. In this embodiment, the activity monitor 100 can come with the bottle 500 or sold separately and use after the bottle is initially opened. Once the stopper with the activity monitor 100 is attached to the cap and the cap is placed onto the bottle, the bottle can then be monitored.

Figure 6:
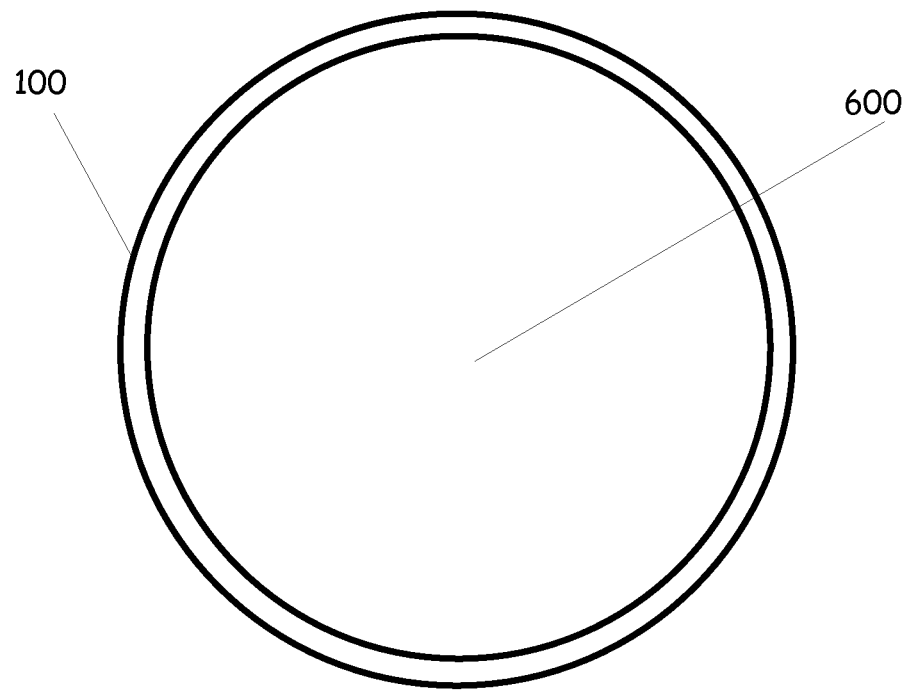
FIG. 6 is a conceptual diagram illustrating an activity monitor with an adhesive connector.

FIG. 6 is a conceptual diagram illustrating an activity monitor with an adhesive connector. In this embodiment, underside of the activity monitor 100 includes an adhesive tape, such as a double sided tape 600 that is attached to the underside of the activity monitor 100. The opposing side of the adhesive tape is typically covered by a plastic coating or shield to prevent the adhesive from inadvertently being attached to a surface or gathering debris. Various other attachment mechanisms may also be used including Velcro or any loop and hook technique as well as similar structures. When the activity monitor 100 is being put to use, the plastic cover can be removed and the activity monitor 100 can be attached to the surface of the container or object to be monitored.

Figure 7:
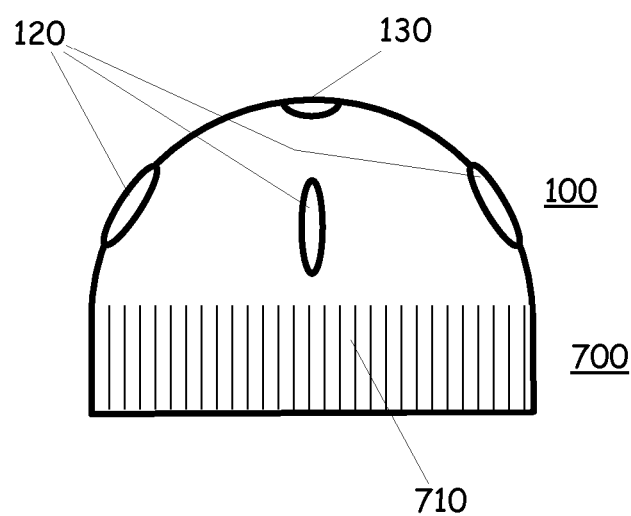
FIG. 7 is a conceptual diagram illustrating an activity monitor built into a cap structure.

FIG. 7 is a conceptual diagram illustrating an activity monitor built into a cap structure. In this embodiment, the activity monitor 100 is integrated into a cap 700 that can be attached to various bottles compatible with the given cap size. As is typical for a bottle cap, ridges 710 may be included on the surface of the cap to facilitate removal and placement.

Figure 8:
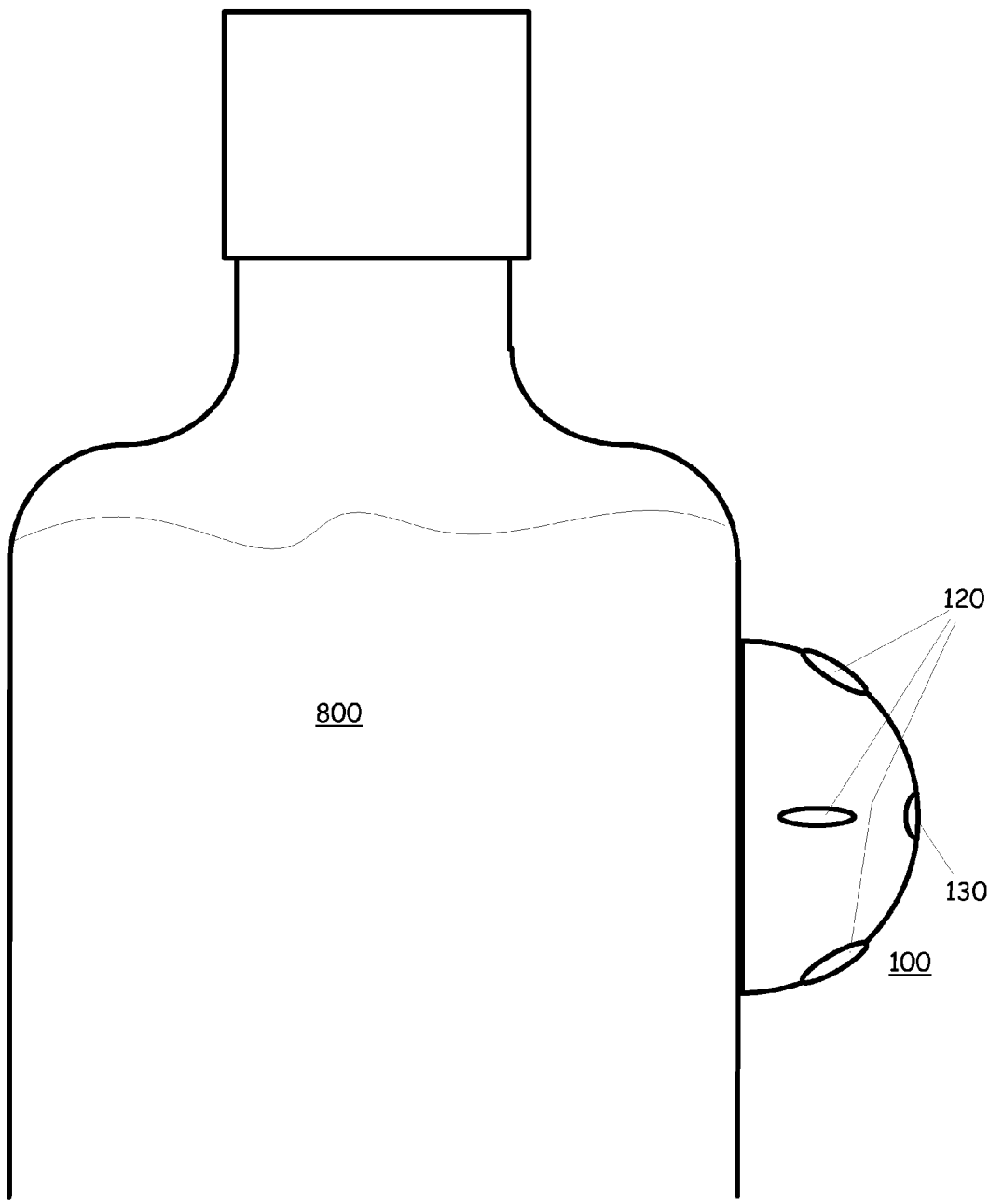
FIG. 8 is a conceptual diagram illustrating an alternate location of attaching the activity monitor to a bottle.

FIG. 8 is a conceptual diagram illustrating an alternate location of attaching the activity monitor to a bottle.

Thus, it will be appreciated that the activity monitor may come in a wide variety of shapes, sizes, forms, configurations etc., and the above-presented embodiments have been provided as non-limiting examples.

Operation of the Activity Monitor

The operation of the activity monitor will be described in three functional stages to facilitate a better understanding. However, it should be appreciated that the functional stages can be mutually exclusive of each other or, in some embodiments two or more stages may coexist on a single activity monitor.

The three stages include: (1) programming; (2) operational; and (3) reporting.

Programming Stage. The programming stage involves the setting up of the activity monitor to perform a desired function. The activity monitor can be provided as a pre-programmed device with fixed, non-changeable settings or, the activity monitor can include a user interface for changing, modifying and programming the operation of the activity monitor. In the former embodiment, the programming stage of the activity monitor occurs during factory construction or, may simply be a default due to memory and/or hardware configurations of the activity monitor. In the latter embodiment, the activity monitor includes a user interface that allows the user to program, modify or configure the operation of the activity monitor.

The programming of the activity monitor configures the activity monitor for a specific application or use. In one embodiment, the activity monitor is set at factory fabrication to include one or more operational configurations. Thus, the activity monitor can be fabricated for different and specific applications. In other embodiments, general purpose activity monitors that include several pre-programmed features can be configured at fabrication. In yet other embodiments, the activity monitor may include configurable features and operations that can be selected and/or adjusted after fabrication, either at the factory or by a distributor, seller, OEM, or user of the activity monitor.

For programmable embodiments, the activity monitor will include an interface for programming the activity monitor, selecting features of the activity monitor, or setting parameters to adjust the operation of one or more features of the activity monitor. The programming interface may range from a rudimentary interface of a few buttons with audible or led light feedback confirmation to an elaborate, PC based application program that configures and programs the activity monitor through a port, such as a wireless port (e.g. 802.11, BlueTooth, Zigbee etc) or a wired port (e.g USB, FIREWIRE, etc). Furthermore, such an application may allow various software downloads into the activity monitor, including software upgrades, selection and activation of desired features, parameter settings, etc. Furthermore, programming can occur from the system level based on information that was obtained based on the customers use pattern. Doctors, pharmaceuticals, children, grandparents, etc. can program the device simply by using the device.

Operational Stage. Once the activity monitor is programmed, it is ready to enter operational stage. However, the activity monitor may remain dormant for an extended period of time before it placed into the operational stage. Also, the reader should understand that even if the operational stage is entered, the programming stage can be reentered at any time for embodiments that allow reprogramming of the activity monitor. The operational stage may be entered or triggered in a variety of fashions. A few non-limiting examples including pushing an "on" button, removing a plastic cover over the battery to allow continuity, removing a cover from a photovoltaic sensor, etc. During the operational stage, the activity monitor monitors various sensors and makes operational decisions based on such monitoring. For instance, the activity monitor may monitor one or more accelerometers, a photovoltaic sensor, biometric sensor, a pressure switch, a magnetic switch, an electromagnetic switch, RFID detectors, user interface buttons etc. During the operational stage, the activity monitor may also record data into its internal memory or, transmit date to an external device over a wired or wireless interface.

Reporting Stage. Upon completion of the operational stage or, at some point after the operational stage is entered, it may be desired to extract data from the activity monitor. this is referred to as the reporting stage. The types of data, frequency of reports, etc. can vary greatly depending on the particular use of the activity monitor. In any case, in the reporting stage the data that is stored internal to the activity monitor or, that has been previously extracted is reviewed and any necessary reports that reflect information about the data can be generated.

Examples of Embodiments

Although the reader will appreciate that a wide variety of uses could be employed for the activity monitor, a few non-limiting examples are provided to illustrate the various capabilities, aspects and functions of various embodiments of the activity monitor.

Medicine Reminder. One feature that may be incorporated into an embodiment of the activity monitor includes the medicine reminder feature. This feature operates to alert a person or a person caring for a person, patient, animal, etc., that it is time to administer a dosage of the medication contained within a bottle. Thus, the activity monitor is attached to the bottle of interest. The activity monitor is programmed to provide an alert at the specific dosage times. For instance, if the medicine is to be taken in 4 dosages throughout a 24 hour period, the activity monitor can be programmed to provide the alert every 6 hours. In some embodiments, the exact hours are fixed (such as 6 am, 12 pm, 6 pm and 12 am) but, in other embodiments the exact hours can be adjusted through the user interface, at the factory or based on the specific times that the activity monitor is used in the learn mode (e.g., 8 am, 12 pm, 5 pm and 11 pm—because this works best with the user's schedule) configuration. When the activity monitor provides the alert, the activity monitor then begins to monitor the bottle activity. If the activity monitor does not detect that the bottle has been tended to, such as the accelerometer detecting that the bottle has been moved or opened, or other sensors in the activity monitor detect activity that indicates the same, then the activity monitor may be programmed to provide an escalating alert notification (e.g., an increasingly louder alarm). If the activity monitor detects that the bottle has been moved or opened, or that medicine has been removed from the container, then the alarm can automatically be reset. In other embodiments, the activity monitor may include a reset button to silence the alert condition and begin the next cycle.

Medicine Alarm. Another feature that may be incorporated into an embodiment of the activity monitor includes the medicine alarm. The feature operates to help prevent over dosages of a medication. For instance, if this feature is combined with the medicine reminder feature, once the activity monitor detects that the medication has been taken, a lock-out timer can be initiated. If the activity monitor detects that the bottle or container has been moved or opened during the lock-out period, an alert can be triggered to notify the user that no dosages are presently due to be administered or taken.

Tamper Detector. Another feature that may be incorporated into an embodiment of the activity monitor includes a tamper detector. As a tamper detector, the activity monitor can be affixed or attached to a variety of items or containers. If the activity monitor detects that the device or container has been moved, opened, jarred, etc., it can record such information as a data entry and/or provide an alert indicator. The tamper detector may also include windows of time at which activity would be considered to be a tamper, and windows of time during which activity is permissible. For instance, liquor bottles in a bar would include a window of permissible activity during working hours but, if the bottle is moved while the bar is closed, this would be considered as a tamper. The tamper detector may be configures such that the entrance of a specific key sequence or authorization code can be used to silence the alarm or exit the alarm state. If the code is not entered properly, the alarm condition continues. Further, rather than simply sounding an alarm, the tamper detector may also include an interface to provide external notification (i.e., POTS, Cellular, Internet, etc.).

Closed-loop Medication Monitor. It will be appreciated that the interaction of medication with an individual can vary depending on a wide variety of circumstances and elements. Such circumstances and elements can include the body weight of the individual, the individual's metabolism, the dietary habits of the individual, the saturation of the medication in the individual, the absorption rate of the medication, etc. For instance, the activity monitor can be integrated into or with other monitors, sensors and devices to provide an overall control mechanism for the administration of medication. As an example, the activity monitor operating as a medicine reminder may be programmed to administer certain dosages of medication at specific times. However, in response to feedback from other sources, such feedback being associated with one or more of the above-identified circumstances and elements, as well as others, the dosage amount and periodicity of the dosage can be modified in real-time. Thus, such an embodiment provides a closed-loop monitoring system that can help to optimize the administration of medications. In addition, the activity monitor, or even multiple activity monitors may be networked together and in communication with one or more remote, distributed or central systems that monitor the activity reported by the activity monitor, as well as information and data obtained from a variety of other sources which may includes, as non-limiting examples, environmental, cost issues, insurance payment issues, doctor recommendations, other medical test results, other prescriptions provided to the user, foods that are purchased or taken by the user, location of the user (for instance is certain substances are banned in certain areas), activity of the user etc. All of this information can be provided to such other systems and processed. For instance, the system may then be operable to send an alert message to an activity monitor or some other designated destination, or even send a lock signal to the activity monitor which can then mechanically lock the container to prevent further access.

To further facilitate the understanding of the various aspects, features and applications of the various embodiments of the activity monitor, a few additional non-limiting examples are provided.

Simplified User Interface. In one embodiment, the activity monitor includes simplified user interface for programming of the medicine reminder function. In the embodiment illustrated in FIG. 1, the activity monitor includes 4 buttons. However, it will be appreciated that the activity monitor can include more or fewer buttons and the 4-button configuration is provided as a non-limiting example only. In the illustrated embodiment, the medicine reminder operation can be set by a user pressing one of the four buttons and holding it down for a given period of time (i.e., 10 seconds) to select the mode of operation associated with the button. If the buttons are labeled 1, 2, 3, 4, pressing and holding the button can activate the medicine reminder to sound an alarm for the selected number of dosages, periodically through a 24 hour period beginning at the current time. Thus, if the user presses and holds the 3 button down for the required period of time, the user will be notified to take a dose at the current time (or this may simply be assumed) and then, notified again every 8 hours that another dosage is due.

In other embodiments, the activity monitor may include intelligence that monitors the activity of the user and adjusts the schedule accordingly. For instance, if the user takes a certain medication regularly, if the activity monitor detects that the user is always 1 hour late for a particular dose, then the activity monitor may adjust the dosage time to more align with the user's schedule. Further, the user may be allowed to program the activity monitor to provide alert notifications at specific times. Thus, the user can have a schedule that is not exactly aligned on a periodic basis but is within prescribed parameters for the particular medication. Further, the schedule may be adjusted due to other factors or data received from other sources. For instance, environmental issues (i.e., atmosphere, temperature, stress levels, sleep quantity/quality, etc) may be used to retard or accelerate the dosage due notice. For instance, in the case of a migraine patient, a sudden change is barometric pressure may trigger an earlier notification to take a drug such as Topamax or a Triptan.

Figure 9:
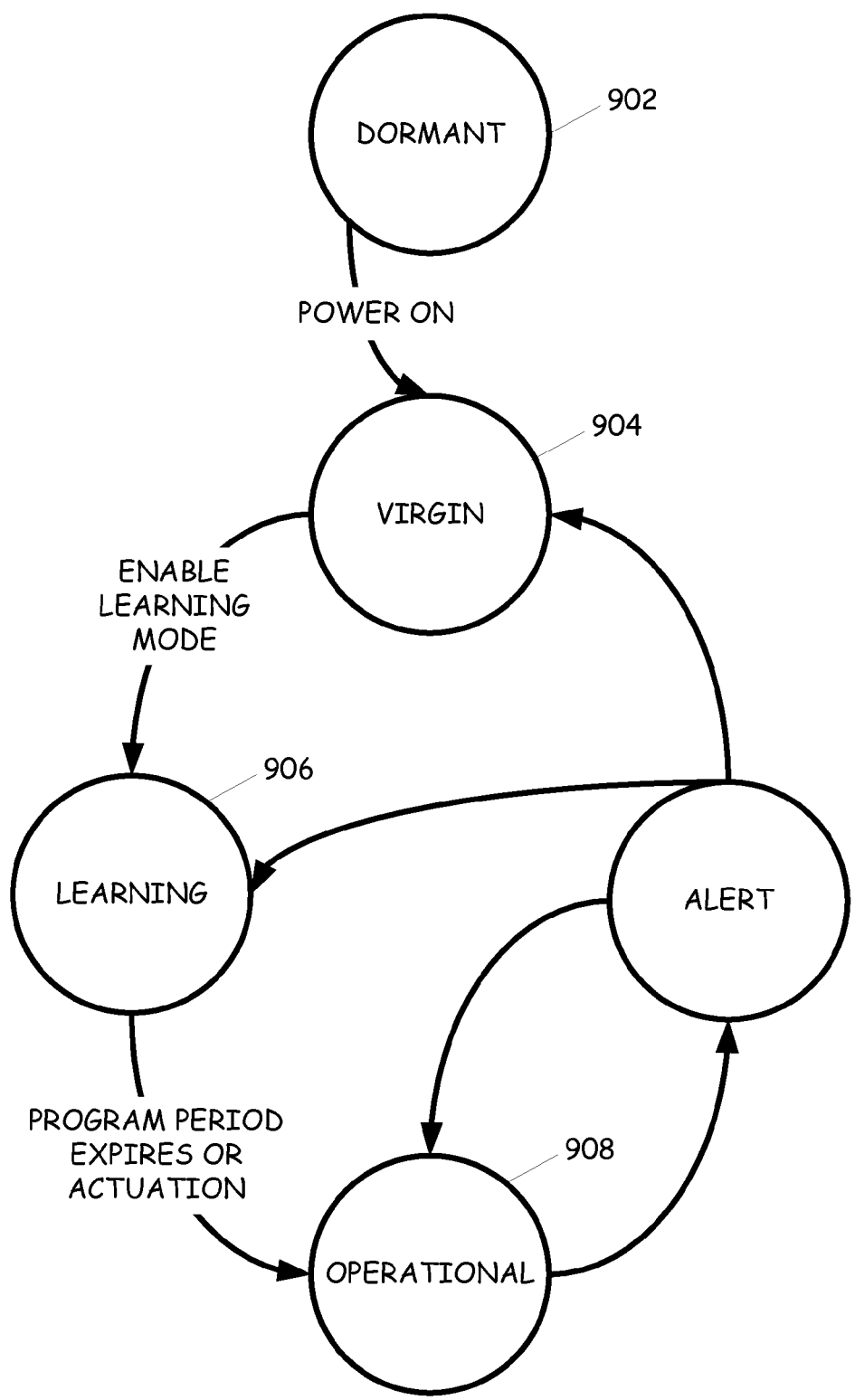
FIG. 9 is a state diagram illustrating the operation of a programmable user interface in an exemplary embodiment of the activity monitor.

Programmable User Interface. FIG. 9 is a state diagram illustrating the operation of a programmable user interface in an exemplary embodiment of the activity monitor. In this embodiment, the activity monitor 100 can be programmed for multiple alerting times (such as four schedules) within a given period of time, typically a 24 hour period. It should be appreciated that although the present example is described as including up to four alert times within a 24-hour period, that any number of alert times over any period of time could also be utilized. For instance, the alerts could based on a time period of a week, 12 hours, or any other time period including varying times between dosages.

In the embodiment being described, a new activity monitor is first resident in the dormant state 902. In the dormant state, the activity monitor does not have any power being applied to the circuitry. To exit the dormant state 902, power is applied to the activity monitor. Applying power can be accomplished in a variety of techniques including, but not limited to, moving a switch, installing a battery, removing a battery isolator plastic strip, or the like. Once power is applied to the activity monitor, the activity monitor transitions to the virgin mode 904.

In the virgin mode 904, the activity monitor has power applied to it but, it has not received any programming information or, has not received the necessary programming details for operation.

The embodiment being described includes a learning mode 906 to facilitate self-programming or assisted programming of the activity monitor. Once the activity monitor is attached to a cap or container, the initial programming is performed by first placing the activity monitor into a "learning mode". In an illustrative embodiment, to enter the learning mode, an actuation by a user is performed. For example, a user may press and hold a particular button, such as the top or center button 130 for a period of time, such as 10 seconds, to cause a transition to the learning mode 906. However, it will also be appreciated that the activity monitor may automatically transition from the virgin mode 904 to the learning mode 906 after being powered up or after a particular period of time. In addition, some embodiments may transition from the dormant mode 902 directly to the learning mode 906.

Figure 10:
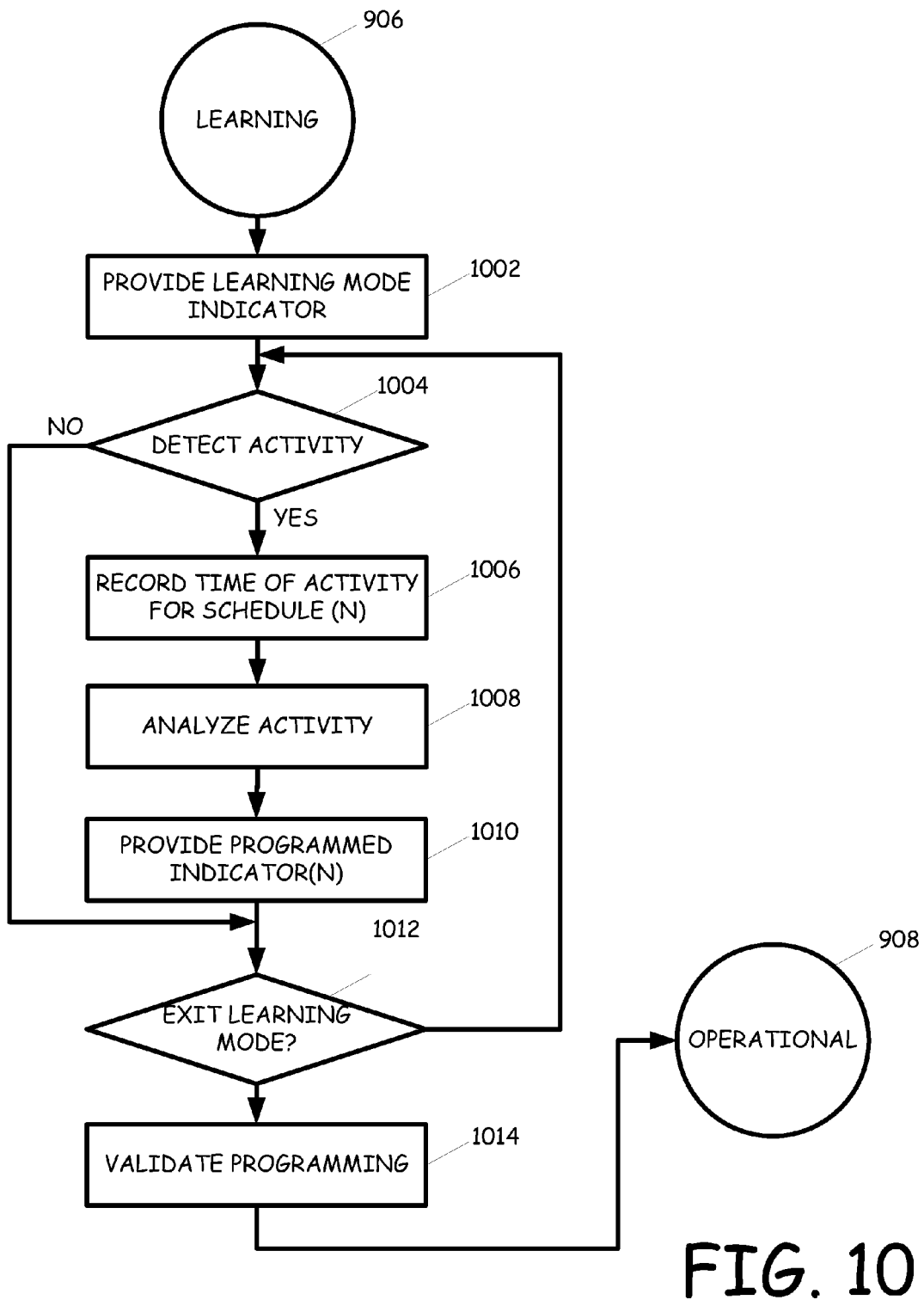
FIG. 10 is a flow diagram illustrating exemplary steps in an embodiment of the learning mode.

FIG. 10 is a flow diagram illustrating exemplary steps in an embodiment of the learning mode. Once the learning mode 906 has been entered, an indicator can be provided as feedback to the user 1002. For instance, to indicate that the activity monitor is in the learning mode 906, the four external LED's 120 can blink, alternating between red and green. When the activity monitor 100 enters the learning mode 906, it resides in this mode for a programming period of time, such as 24-hours. During the programming period, the activity monitor monitors the use of, and memorizes/records the use of the container associated with the activity monitor.

In a typical learning mode 906, a loop can be entered to program one or more schedules based on activity associated with the container. Initially the activity monitor looks for the detection of activity 1004. The first time that the container is opened, accessed or moved within the programming period while learning mode is active, the activity monitor records the time of the activity and associates the time with the program for schedule 1. For instance, in a particular embodiment, if activity is detected 1004, then the time of the activity is recorded for one of the available schedules (such as the next incremental schedule(n)) 1006. Prior to accepting the activity as a valid programming, the activity monitor may conduct an analysis of the activity 1008. The analysis applies heuristics or rules to verify that the activity detected actually constitutes a programming request. The heuristics may include a variety of rules or criteria. A few non-limiting examples include:
(a) is the activity too proximate to other recent activity
(b) did the activity meet a threshold activity level, was it too short to constitute an opening, was it too long, etc.
(c) is the current time an increment of previously stored schedule times?
(d) automatically suggesting activating specific times of use based on the med type, information received from the doctor and systems and info from the sleeping patterns, etc.

Once the activity monitor accepts the activity as a programming action, the program schedule is update and an indicator that schedule(n) has been programmed can be provided through indicator(n) 1010. Thus, the time of the activity may be stored in a memory location associated with a first schedule, with each of the LED's on the activity monitor being associated with a schedule as well. After programming the first schedule, the first LED is changed to represent that the programming for that schedule has been accepted and is complete. For instance, the LED may change from alternating between red and green to being a solid green, or simply flashing green. The remaining LED's on the activity monitor continue blinking to show that learning mode is still active.

The activity monitor then determines if the learning mode should be exited 1012 and if not, processing continues at step 1004. At this point, it should be appreciated that if the activity monitor is being programmed for a medication that is only taken once a day, then there are no further steps necessary and the learning mode can be exited. At the end of the programming period, the learning mode will be exited with only one schedule being programmed. However, the user should be careful not to take the medication the following day any sooner than a trigger threshold from the first administration to ensure that the activity monitor is not confused as to whether this is a second dosage in the cycle or the beginning of a next cycle. In some embodiments, the activity monitor may query the user to resolve such a conflict.

In addition, some embodiments may also include an actuation mechanism to exit learning mode. For instance, the same actuation used to enter the learning mode, or some other actuation, may be used to exit the learning mode. As a specific example, when the learning mode is active, the user may exit the learning mode by either allowing the programming period to expire or, by manually exiting the learning mode (i.e., pressing and holding the center button 130 for 10 seconds as a non-limiting example).

For medications or items that are taken multiple times per day or per programming period, the user simply takes such content at the necessary times as prescribed/desired during the initial programming period while in the learning mode is active. The activity monitor detects activity associated with the container and, if it concludes that a dosage has been taken, the activity monitor records the additional scheduled times of use in the other scheduled time periods. For any schedule period that is not scheduled after the initial programming period learning mode (e.g. schedule #3 and schedule #4 in an example where the user takes dosages only twice daily) the LED's will be clear indicating that there is no activity associated with those schedules.

Thus, the learning mode can be exited 1012 in a variety of manners including, but not limited to, the programming period expiring, the user actuating an exit button or the conclusion of programming each of the available schedules.

Prior to exiting the learning mode, the activity monitor may perform a validation step 1041 to ensure that the programming information is correct or is logical. The activity monitor can look at the above-identified heuristics as well as other heuristics to determine if the program entries appear to be a valid program. For instance, if three schedules are entered in 6 hour increments and a fourth schedule is programmed two hours from the third schedule, the activity monitor may trigger a programming alert to the user. Depending on the embodiments of the invention, the programming alert may simply flash indicating that the programming is invalid and needs to be reprogrammed or, a more elaborate user interface may be employed to indicate what the questionable programming entries are and allow the user to remedy or override.

Figure 11:
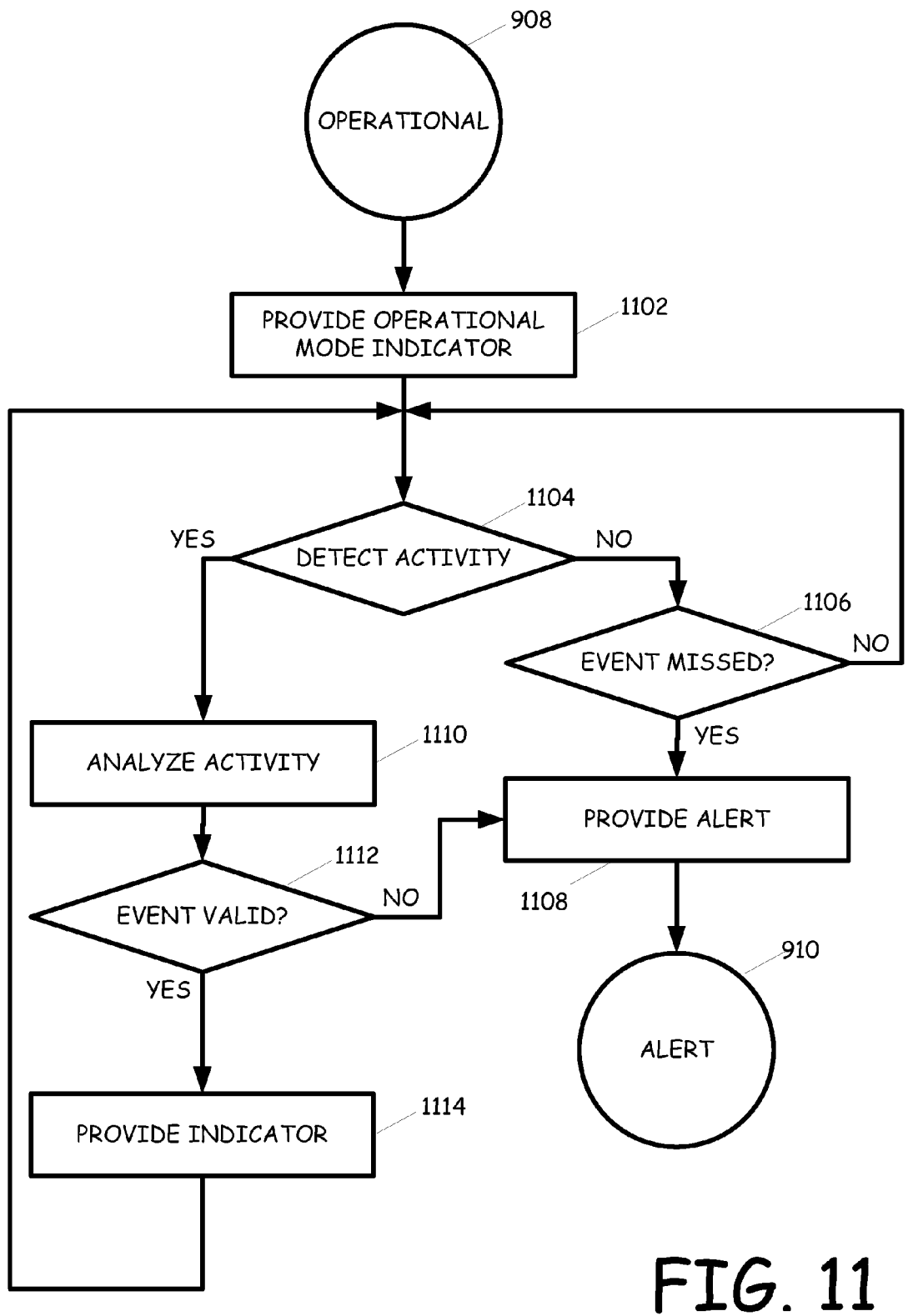
FIG. 11 is a flow diagram illustrating typical steps in an exemplary operational mode.

After the initial programming period, the activity monitor exits the learning mode 906 and enters operational mode or monitoring mode 908. In the operational mode 908, the activity monitor monitors the activity associated with the container in view of the program schedules. By applying a set of heuristics or rules, the activity monitor makes a determination as to whether or not compliance with the programmed schedules appears to have occurred or if action needs to be taken. FIG. 11 is a flow diagram illustrating typical steps in an exemplary operational mode.

Initially, the activity monitor 100 may provide an indicator that the activity monitor is in operational mode 1102. The operational mode 908 indicator can be presented in a variety of manners, such as a constantly illuminated LED, a flashing sequence of LED's or the any of a variety of other techniques. Similar to the learning mode 906, the operational mode 908 then looks for the detection of activity associated with the container but, the operational monitor loop also looks at the program schedules. In the illustrated embodiment, the activity monitor 100 seeks to detect activity associated with the container 1104. If activity is not detected the program scheduling is examined to determine if an event has been missed 1106. If an event has been missed, an alert indicator is provided 1108 and the alert mode 910 is entered. As a specific example, if a user fails to remove the cap of a container within a threshold period of time after a scheduled time (i.e., 15 minutes as a non-limiting example), the activity monitor provides an alert indicator and then enters an alert mode 910. In addition, the LED in the schedule period in which the cap has not been opened will blink RED further indicating that the content has not been taken.

If activity is detected 1104, then the activity is analyzed in view of the afore-mentioned heuristics and rules, as well as others, in view of the program schedules 1110. If the activity is valid and is associated with a valid, scheduled event, then a indicator may be provided that the programmed event has been satisfied 1114 and processing continues at step 1104 to monitor additional activity. However, if the detected activity is not valid or associated with a valid event, then the activity monitor may trigger a tamper alert and provide an alert indicator 1108 as it transitions into the alert mode 910. As an example, one embodiment of the activity monitor may by default, monitor the use of the cap during the scheduled times and transition to an alert mode if the cap is removed more than 30 minutes prior to a scheduled period. In one embodiment, the activity monitor, when entering tamper alert mode, may chirp rapidly and loud and flash the LED, indicating that the cap has been removed outside of the scheduled periods of use. In other embodiments, a silent alarm may be employed so that only the valid user knows that the container has been tampered. In yet other embodiments, a signal may be sent to another device, such as a cellular telephone or pager through any of a variety of transmission techniques, to sound an alarm or provide a tamper alert indicator. It will be appreciated that a wide variety of alerts can be provided in the various embodiments. A few non-limiting examples include pre-recorded phrases, sound clips, ring tones, buzzers, tones, vibrations, pings, or the like.

As previously described, the alert mode may be entered due to a missed scheduled event or due to a tamper event. Other alert modes may also be defined and employed in other embodiments of the activity monitor. In the described embodiment, the alert mode can be reset or exited if the alert was caused by a missed event. However, if the alert was caused by a tamper, the activity monitor cannot be reset or, can only be reset by entering a pass code.

To exit the alert mode, the user must actuate the device. In one embodiment, the alert mode 910 may be exited simply by opening the container and taking the medicine dosage. In other embodiments, one or more buttons can be pressed and held for a period of time to cause a transition out of the alert mode 910. Various exit means may also be used if it is desired to have the activity monitor exit to a desired state. For instance, the activity monitor may exit to the virgin state 904 in response to one actuation, the learning mode 906 in response to a second actuation and the operational mode 908 in response to a third actuation.

If the alert mode 910 was entered due to a tamper event, the user may be required to not only actuate the activity monitor, but then in response to a prompt, enter a pass code to allow transition from the alert mode. As an example for the embodiment presented in FIG. 1, a user may be required to press and hold the center button for 10 seconds to initiate a transfer out of a tamper event triggered alert mode. The activity monitor may then provide an indicator, such as flashing LED's and/or a sound to indicate that the user must provide the pass code. The user may then enter a sequence of buttons 120 that satisfies the required pass code. It should be appreciated that the pass code may be factory set and provided to the user along with the activity monitor or, the pass code can be programmed by the user in virgin mode 904 or the learning mode 906. As another example, to exit a tamper alert mode, the user may be required to remove the cap and place it on the counter for 30 seconds making sure it's stationary for at least 30 seconds. Next the cap can be replaced on the container and then by pressing and holding the center button for a prolonged period of time (i.e., 15 seconds). (In another embodiment, an external device may be required to cause the activity monitor 100 to exit the tamper alert mode. For instance, a key may physically be entered into the activity monitor to reset the tamper alarm or, a signal from an external device, such as a cellular telephone, RFID tag, etc. may be used to reset the tamper alert mode.

One embodiment of the activity monitor is a tamper detector. In this embodiment, the activity monitor can be used exclusively to monitor the inappropriate or unauthorized use of any bottle with a cap, such as prescription drugs, alcohol, sodas in the fridge for children on special diets, etc. To program activity monitor to operate exclusively in a tamper alert mode around the clock (i.e. no programmed schedules) the activity monitor is placed into the learning mode. An indicator is then provided to the user, such as the LED's blinking and alternating from red to green indicating it's in the learning mode. While in the learning mode, the activity monitor may then be set to operate as a tamper detector only using a variety of techniques. In other embodiments, the activity monitor may come factory set to only operate as a tamper detector.

As a non-limiting example, for the above-describe embodiment that includes 4 program schedules, a tamper only monitor mode can be invoked by using the following programming sequence:

(1) attach the activity monitor to the container
(2) set the container down in a stable and stationary position for a threshold period of time, the time of 30 seconds is used as a non-limiting example throughout this procedure
(3) remove the cap and place the cap on the counter for 30 seconds making sure the cap is stationary—after 30 seconds, LED #1 will turn green
(4) place the cap back onto the container and wait 30 additional seconds making sure the cap and container are stationary
(5) open the cap again repeating the process 3 more times by opening the cap and replacing the cap as described above. Once programmed in the tamper alert mode, all of the LED's will blink green 5 times and then they will be clear indicating that the tamper detection mode has been successfully programmed to monitor any use of the cap at any time.

At this point, if activity is detected, the activity monitor will enter the tamper alert mode. It will be appreciated that a variety of other techniques can be used such as pressing and holding certain button combinations, or entering certain button sequences.

In a computer interface enabled embodiment of the present invention, the activity monitor can be communicatively coupled to a computer for programming. In such an embodiment, a wireless technique or a wired technique may be utilized. An application program may be presented on the computer to identify the connected activity monitor and provide programming instructions and capabilities for the activity monitor. In addition, the programmed schedules can be read from the activity monitor for evaluation, and the historical activity of the activity monitor may be accessed and analyzed.

In a particular embodiment of the present invention, the activity monitor may be programmed at a pharmacy at the time medication is dispensed to a customer. Thus, the pharmacist can program the activity monitor in accordance with the doctor's prescription. Similarly, the activity monitor can be programmed at the doctor's office and provided to the patient. For example, the activity monitor can be programmed automatically based on the type of drug and the information received from the doctor (i.e., which may have been sent provided automatically to the pharmacist,) as well as, or pre-provided or presently provided user preferences.

One aspect that can be incorporated into various embodiments of the activity monitor is a "buy-now" or "order-now" feature. This feature provides a button on the activity monitor that can be pressed to trigger and initiate an order for a refill. For example, the activity monitor may be provided with the prescription information stored within its memory. Further, the activity monitor may be wireless tethered to an Internet connected device, such as a BLACKBERRY or IPHONE. When the "buy-now" button is pressed, prescription information may be read out of the activity monitor and then transmitted to the user's pharmacy requesting a refill or to the doctor's office requesting a renewal of the prescription. Similarly, the activity monitor could be utilized with a variety of consumables and operate to provide such notice to a user with regards to a need to purchase additional quantity.

Another aspect that can be incorporated into various embodiments is the feature of sending alert messages to various devices and individuals. For instance, for an elderly person, if an alert condition is detected, a message may be sent to the user's children to notify them to come and check on their parent. The messages can be sent in a variety for forms, such as pages, text messages, twitter postings, facebook postings, email messages, etc.

In addition, the activity monitor may send alert messages to indicate that it is time to take a dose of medicine. For instance, the activity monitor may send a text message, email message, or any other variety of messages to a user's device, such as a cellular telephone, PDA, IPHONE, etc. The user is then notified that it is time to take his or her medication.

Prescription Monitor. Various embodiments of the activity monitor are ideal solutions for the issues surrounding prescription drug abuse as presented in the Background section. This is a serious issue that is getting much attention in our nations. Imagine what our world would be like today if we still had Marilyn Monroe, Jimmy Hendrix, Elvis Presley, Bruce Lee, Keith Moon, Steve Clark from Def Leppard and Margaux Hemingway, as well as many others that have died from the abuse of prescription drugs. Various embodiments of the activity monitor can be used to detect, record, report and prevent prescription drug abuse.

In general, the activity monitor can be used to detect the administration of medicine, as well as dosages. Information regarding the use of a substance can be recorded and stored within an activity monitor. This information can then be accessed by an authority or some entity to determine if there is a suspicion of abuse related to the subscription. To further describe this aspect of the activity monitor, various examples are provided.

In one embodiment, when an individual is issued a prescription, the activity monitor can be included along with the medication. The activity monitor can be programmed with the particularities of the prescriptions, such as dosages, timing intervals, etc. As the activity of the container is recorded, the history of the usage is obtained. Each time the container is opened and/or medication is removed (volume changes) can create an entry in the history. Each entry may include a time stamp. This history can be compared to the internally stored programming information for the particular subscription to determine if the medication is being taken properly or, if there is a suspicion of abuse.

In some embodiments, the activity monitor may be paired with a signature device that must be worn by the individual receiving the prescription. In operation, when the activity monitor detects that the monitored device is open, it will search for a signature by sending a probe or looking for a signal (i.e. such as the technology employed in an RFID tag). If the signature device is not detected, then this is an indication that the container was opened by an unauthorized person. In the case of a nurse or care provider, multiple signature devices can be deployed and programmed into the activity monitor. The signature device can be fastened to an individual by means of a break-once bracelet that would verify that the individual has taken the signature device off. In other embodiments, the activity monitor may be attached to the individual similar to a house-arrest anklet, embedded in a microchip under a person's skin or otherwise.

In other scenarios, any individual adjudicated or identified as an abuser maybe required to wear a signature device. In such scenarios, any container equipped with an activity monitor can probe for any signature devices nearby and record the proximate signature devices. The activity monitor can thus be used to detect and report illicit behavior.

If the activity monitor detects suspicious activity, this information can be stored in the activity monitor for future access by others. For instance, in one example, a patient can be required to bring the particular container and activity monitor to the pharmacy when obtaining a refill. During the refill process or prior to approving of the refill, the history information can be read back out of the activity monitor and analyzed. If the pharmacist determines that there is suspicious activity (i.e., excessive use, irregular use, missed dosages, etc), the pharmacist can approach the patient to review the history and, the prescription can be denied if the patient is not able to provide acceptable explanations as to the suspicious activity. For instance, the patient may be referred back to his doctor or a specialist to review the history and determine what actions, if any, are to be taken.

In another embodiment, the activity monitor may include a wireless transmitter that is able to communicate in at least a single direction to a remote server system. As activity is detected by the activity monitor, this information can be relayed back to the server system for recordation and analysis.

Figure 12:
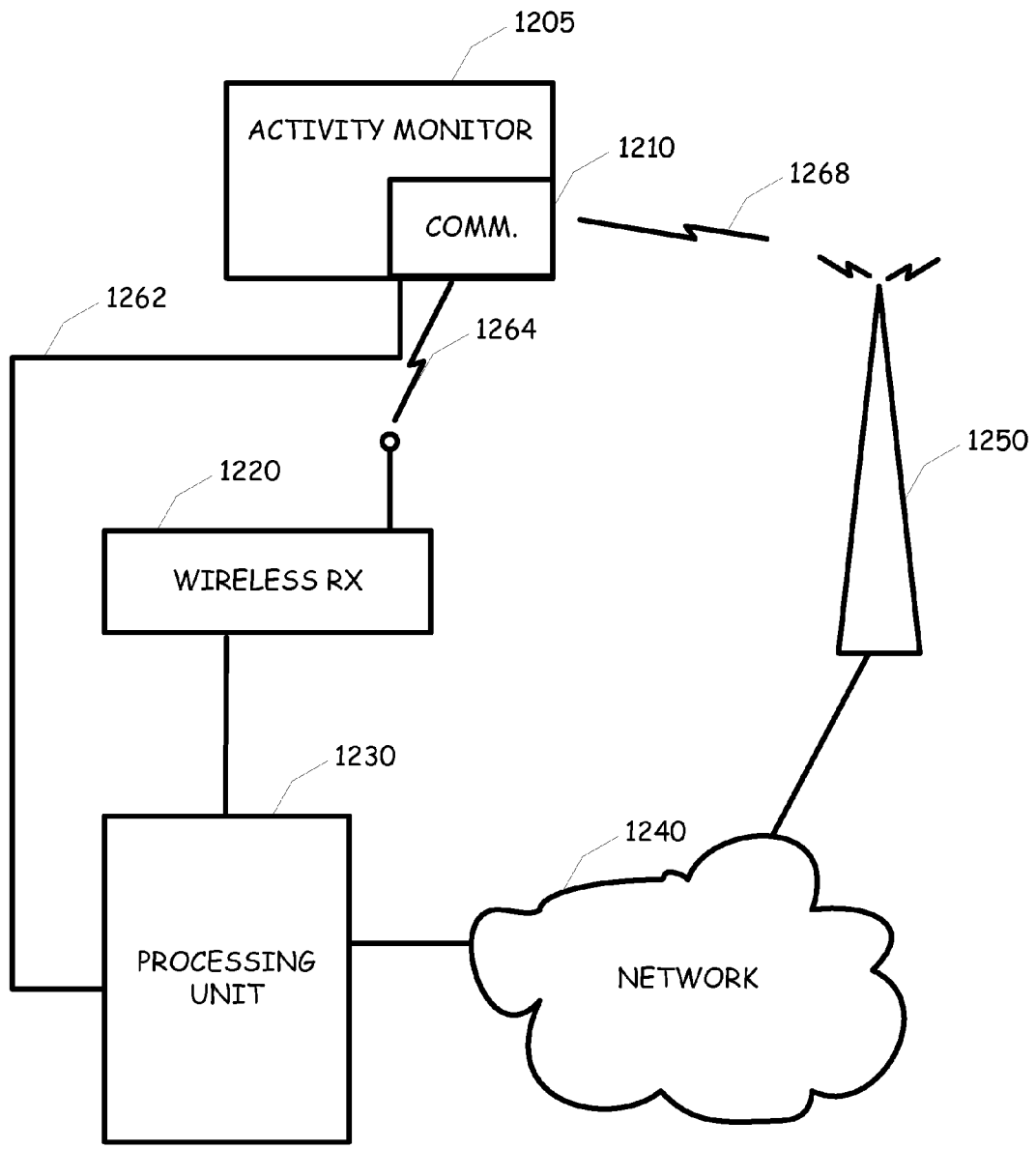
FIG. 12 is a block diagram illustrating an exemplary embodiment in which an activity monitor may operate.

FIG. 12 is a block diagram illustrating an exemplary embodiment in which an activity monitor may operate. The activity monitor 1205 is shown as to include a communication module or function 1210. This communication module may support any or any combination of a wide variety of communication capabilities including, as non-limiting examples, wired USB interface, RS232, FIREWIRE, any 802.11 variety, optical, cellular, or any other variety of wired, wireless, optical etc. For example the activity monitor 1205 can communicate information to a local processing unit 1230 (such as a server, computer, etc.) through a wired interface 1262. The activity monitor may communicate to the same local processor unit 1230 through a local wireless connection 1264 through wireless receiver 1220. The activity monitor 1205 may communicate with a wider range wireless technology, such as cellular, digital cellular, 3G, 4G, GSM, GPRS, CDPD or the like over path 1268 to a wireless receiver 1250. In addition, the activity monitor may include a GPS receiver for recording the location at which the detected activity occurred. The communication of the activity monitor 1205 may also be carried forward to a network 1240, such as the Internet, to provide information to other systems. In some embodiments, the communication may be one direction—from the activity monitor out—but, in other embodiments the activity monitor may also include a receiver for receiving communicated information.

In embodiments that include an 802.11 wireless communication capability, the device can be set up to automatically detect the networks of the patient's pharmacy and doctor such that if the patient brings the activity monitor and container within the vicinity of their doctor or pharmacists, the activity monitor data can be automatically downloaded.

Figure 13:
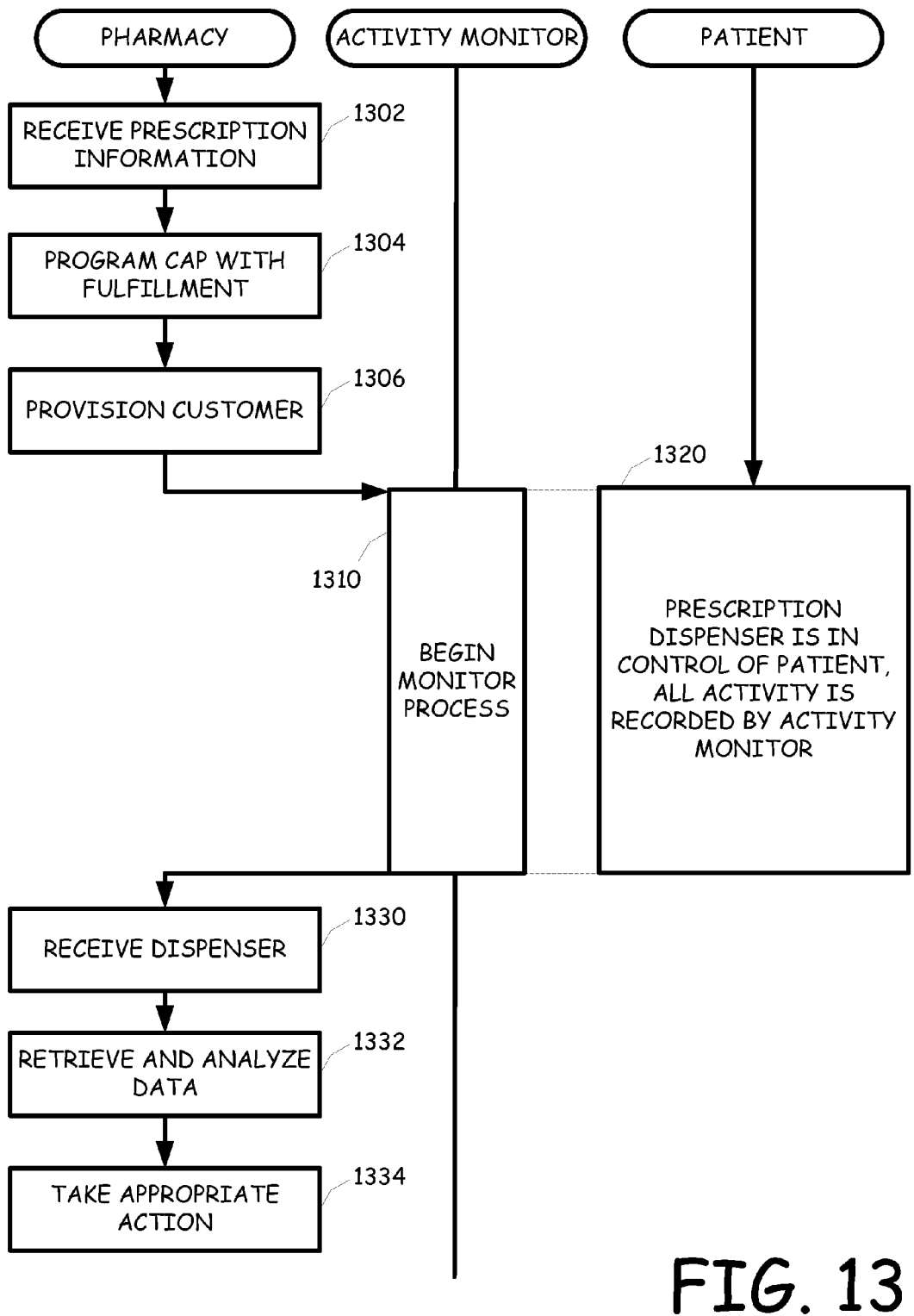
FIG. 13 is a flow diagram illustrating actions that can occur in an exemplary deployment of an activity monitor for detecting prescription drug abuse.

In operation, the activity monitor can be programmed when attached to a container containing an issued prescription. FIG. 13 is a flow diagram illustrating actions that can occur in an exemplary deployment of an activity monitor for detecting prescription drug abuse. For instance, as is typical in the industry, a doctor will write a prescription for a patient and the doctor's office either sends the prescription to the patients pharmacy or the patient hand carries the written prescription to the pharmacy. Upon reception and verification of the prescription 1302, the pharmacist can program and attach the activity monitor to the container 1304 and provide the fulfilled prescription and activity monitor equipped dispenser to the patient 1306. When the activity monitor equipped dispenser is provided to the patient, the monitor is turned on and the activity monitor begins to detect and record activity related to the dispenser 1310 1320. It should be noted that the dispenser may be a typical medicine bottle with the activity monitor attached thereto, or the activity monitor may take the form of a cap on the bottle.

In addition, in some embodiments the activity monitor and the container maybe integrated elements such that once a substance is placed into the container and the container is closed, the patient cannot gain access to the contents but through a dispensing function in the bottle. As a non-limiting example, the dispenser may enable the dispensing of only one pill at a time by including a mechanical or electro-mechanical system that would allow only one pill to be dispensed. This could be implemented by having a two walled chamber access in which the chamber is sized such that one dosage of the medication can fit inside the chamber. The dispenser can then be manipulated to ensure that a dosage has entered into the chamber. For example, if the chamber is in the top of the dispenser, the dispenser can be turned upside down and shaken to get the dosage of medication into the chamber. Once the dosage is loaded into the chamber, a button can be actuated causing an interior door of the chamber to shut and an exterior door of the chamber to open thereby providing access to the dosage. Thus, such an embodiment can ensure that only one dosage of medication is retrieved at each access without having to monitor the volume as in previously described embodiments. Those of ordinary skill in the art will appreciate that such a dispenser could be created in many different configurations and employing a variety of techniques but, the monitored dispenser embodiment is not limited to any particular implementation. Rather, any container or dispenser that provides the ability to monitor and control the dispensing of the medication to control and detect abuse could be utilized in the various disclosed embodiments.

In another embodiment, rather than measuring or controlling volume, the activity monitor may include strain gauges or weight detectors. For instance, the buttons on the activity monitor, or additional actuators, can be placed on a table and used to measure the weight of the container. The change in weight can be used to determine how much of the contents were removed at each activity occurrence. Thus, after each access, the device may prompt or require the user to place the container on a flat surface with the sensors facing down. Once the weight measurement is taken, the information is stored within the activity monitor. Failure to allow such a measurement may also be recorded.

The activity monitor can then begin monitoring the container to detect any activity that can be indicative of a dosage of the medication being taken 1310 1320. The activity monitor records any detectable events of the patient 1320 along with a corresponding time stamp into its memory. It will be appreciated that in addition to a process used to detect and record activity to monitor abuse, any of the previously described features, functions and embodiments may also be included along with this feature. For instance, if the dispenser is accessed and/or a dosage is removed prior to the authorized time, the activity monitor may record this in memory as an event, sound an alarm, send a message to the patient, send a message to the pharmacy, etc. However, the advantage of the recorded information is that it can silent observe and record information that can clearly indicate if the medication is being taken as prescribed.

Figure 14:
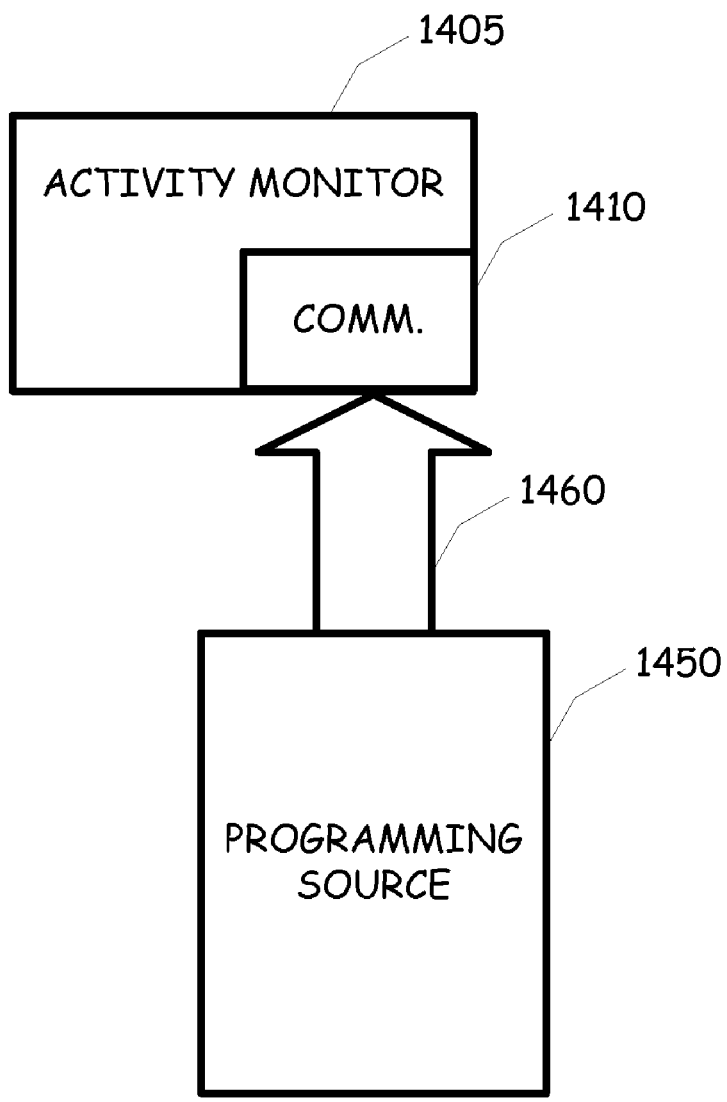
FIG. 14 is a block diagram illustrating various embodiments of a programming environment for an activity monitor.

FIG. 14 is a block diagram illustrating various embodiments of a programming environment for an activity monitor.

In the illustrated environment, an activity monitor 1405 includes a communication interface 1410. A programming source 1450 interfaces with the activity monitor 1405 over a communication channel 1460. It should be appreciated that the programming source can be any of a variety of devices such as a dedicated device, a webpage accessible via a browser, a point of sale terminal at a pharmacy, a computing device at a doctor's office, probation officer's office, recovery program sponsor's office, etc. The communication channel 1460 can likewise be any of a variety of channels including wireless, optical, RF, Bluetooth, WIFI, etc. In operation, the programming source can provide an interface to allow the activity monitor to be programmed for various forms of operation as presented throughout this description.

Today, absent the presently described embodiments, when a patient approaches the pharmacy at the standard refill time, the pharmacist must assume that the medication was taken as prescribed. However, with the activity monitor, the patient can be required to bring the dispenser with the activity monitor back to the pharmacy for a refill 1330. The recorded data can then be retrieved and analyzed by the pharmacist or other authorized party 1332). Based on the analysis of the recorded data, appropriate actions may be taken. For instance, if the recorded data indicates the medicine has been properly taken, the pharmacist may refill the prescription. However, if the recorded data indicates that there has been suspicious activity, then the fulfillment of the refill may be denied or postponed 1334. As a non-limiting example, if the recorded data indicates that the container was only opened a subset of the number of authorized times, this can be flagged as suspicious activity (i.e., more medication was taken out for each access than should have been). Further, if the recorded information indicates that the container openings occur too frequently and without sufficient delay between accesses, this can also be flagged as suspicious activity. In addition, body sensors may also be used in conjunction with the various embodiments. The body sensors can be used to monitor the presence of the medication within the individual. If the body sensor does not detect that the medication is actually present in the user, this may flag an abuse. When such suspicious activity is detected, the pharmacist may require the patient to return to his doctor to renew the prescription or take other counter measures.

It should be appreciated that the activity history stored within the activity monitor may be access by an external system in a variety of manners as previously described. However, in some embodiment, the activity monitor may include a screen or display. In such embodiments, the activity history may be accessed and displayed on the screen or display. In other embodiments, an external display may be connected to the device to allow the activity history to be read.

Such embodiments of the activity monitor may also be used for performing drug screenings by employers, government workers issuing public funds to individuals, etc. For example, the potential individual may be required to bring all prescription medications into office where the screening will take place. For the appropriately equipped containers, the screener can access the data on the activity monitors and determine the likelihood of substance abuse based on this information.

In some embodiments, the activity recorder of the activity monitor may allow for patient interaction. For instance, as a non-limiting example, each time the container is opened and/or it is detected that a dosage was taken, the activity monitor can send an SMS or email to the patient identify what activity has occurred and when the activity occurred and request the patient to confirm receipt, validity and provide further information regarding the activity point. This feature advantageously invokes a report or notice to the patient that an unauthorized access of the medicine container has taken place. Further, the patient can then provide a responding email either confirming or denying knowledge of the event and providing further information related to the event. For instance, if the patient opened the wrong bottle and then, the patient realized that he or she opened the wrong bottle prior to taking a pill, this may trigger an email to the patient. The patient can then explain why the container was opened and confirm the current inventory.

In some embodiments, the activity monitor may also include a locking mechanism. As previously described above with regards to a controlled dispenser, the lock-out mechanism may permanently prevent the patient from opening the container and require the use of a dispenser mechanism. In other embodiments, the lock-out may only be activated when suspicious activity is detected. For instance, if it is detected that a dosage was taken too early or too many items were removed, the lockout mechanism may trigger to prevent further access to the contents. In such an embodiment, the patient may be required to take the container back to the pharmacy to have the lock-out mechanism reset. At such time, the patient can be queried regarding the activity. In other embodiments, the lock-out mechanism may be triggered between dosages such that access to the contents is prevented until within a threshold period of the next dosage and, re-triggered after the dosage is taken or after another threshold period of time after the scheduled dosage. The lock-out mechanism may also require the entrance of a password, finger print, voice recognition, etc., to reset the lock-out. Thus, in such an embodiment not only is activity monitored, but the contents can only be accessed by the appropriate party. The lock-out mechanism can be implemented in a variety of techniques. A non-limiting example of a lockout mechanism would be employing an interior locking mechanism similar to a DVD case that internally locks down. Such an embodiment can prevent cap rotation and removal until a password or required activity is performed.

In some embodiments, the detection/monitor device may be required by a court order. For instance, for an offender, the court may order the individual to utilize monitoring devices for all of their prescription drugs. The individual may be required to report periodically for a download of the historical use of the monitoring device. If abuse is detected then the individual may be incarcerated.

It will be appreciated that such protection mechanisms may also give rise to a risk to patient health. For instance, if a patient is prevented from accessing his or her medication, serious harm may occur. As such, a mechanism to override the lock-out feature may be necessary. An override capability may be implemented in a variety of manners. In one embodiment, any pharmacy or doctor may have access to a "super user" code or override code that would give them access to any container and override the lockout mechanism. In another embodiment, the activity monitor may be equipped with a tone receiver that can detect the reception of a required unlocking tone or tonal sequence and disable the lock-out mechanism once received. For instance, if an emergency arises, the patient may call 911 or another dedicated number that may be published on the container, explain the circumstances and once approved, the called party can transmit the tone or tonal sequence over the telephone line. The patient can hold the bottle next to the speaker of the telephone to have the tone or tonal sequence detected.

It will also be appreciated that various mechanisms may be used to detect access to the container. As previously described, one or more accelerometers by be used to detect movement, such as the removal of a cap. However, other mechanisms may also be employed. For instance, a mechanism may be used to detect cap rotation and direction of rotation. Such a detector can be used to detect opening and closing of the container. As an example, the cap may include a magnet and the container include a series of magnets or metallic surfaces, with spaces between each surface. As the cap is rotated, movement of the magnet past the other magnets or metallic surfaces can be detected and thus detect the presence and direction or rotation. Similar, optical detectors with spaced apart apertures or other mechanisms may also be employed.

Insurance Requirements. The various embodiments of the present invention may be provided in conjunction with insurance programs. For instance, an insurance company may require their customers to have activity monitor dispenser issued for all prescriptions or for certain drugs. The insurance company may provide premium discounts or prescription discounts in exchange for the customer agreeing to receive monitored prescriptions. Further, the information collected may be used to offer further discounts to customers with good history or, used to increase the premiums for customers that consistently show suspicious activity. It will also be appreciated that many insurance companies allow the fulfillment of prescriptions by mail. The various embodiments of the activity monitor may also be used in these circumstances. For instance, the medications can be delivered with an activity monitor. In an exemplary embodiment, the activity monitor may have a lock-out mechanism initially triggered and the patient may be required to perform an activity to have the lock-out mechanism reset. For instance, the patient may have to call a particular number to obtain a code, receive a tone or tonal sequence, connect the activity monitor to his or her computer and access a monitor website that can down load information to and from the activity monitor over the Internet, program the activity monitor and/or reset the alarm.

In other embodiments, the patient may be issued one or more activity monitors that must be attached or used in conjunction with received medications. The patient may be trusted to attach the activity monitor to the received medications or, the received medications may be physically locked down until the activity monitor is attached.

In some embodiments, the activity monitor may simply include accelerometer(s) to detect movement. However, in other embodiments the activity monitor may include more complex technology to measure volumes of material within the container. In such an embodiment, the activity monitor can effectively notify a user when the dosage taken was too small, too large or just right. In addition, this embodiment of the activity monitor can detect when the contents are getting low and initiate or alert that it is time to refill the prescription. For instance, the activity monitor may include a sensor, such as a depth finder technology sensor, that can be used to determine the volume of contents. When the activity monitor is first installed, the sensor conducts an initial volume check. After each subsequent opening, the sensor again checks to content volumes. If an unusual change in volume is detected, or if no change is detected when a change was expected, and alert can be provided.

The activity monitor can be provided and marketed in a variety of manners. For instance, in one embodiment, the activity monitors may be disposable devices that are thrown away with the empty medicine bottles. In such an embodiment, programming can be simplified as the device will be used with only one medicine for a limited period of time. In such an embodiment, the activity monitor may be sold by itself, or in groups, such as 4 packs and 6 packs, with the batteries already installed but disabled by use of a plastic isolating strip that can be removed when desired for operation. In other embodiments, the activity monitor may include a replaceable or chargeable battery and can be reused and reprogrammed multiple times.

In the description and claims of the present application, each of the verbs, "comprise", "include" and "have", and conjugates thereof, are used to indicate that the object or objects of the verb are not necessarily a complete listing of members, components, elements, or parts of the subject or subjects of the verb.

In this application the words "unit" and "module" are used interchangeably. Anything designated as a unit or module may be a stand-alone unit or a specialized module. A unit or a module may be modular or have modular aspects allowing it to be easily removed and replaced with another similar unit or module. Each unit or module may be any one of, or any combination of, software, hardware, and/or firmware.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

It will be appreciated by persons skilled in the art that the present invention is not limited by what has been particularly shown and described herein above. Rather the scope of the invention is defined by the claims that follow.

What is claimed is:

1. A method for an insurer to help alleviate an abuse of controlled substances by insured individuals that pay a premium for insurance to the insurer, the method comprising the actions of: the insurer offering a discount for controlled substances that are distributed in conjunction with the activity monitor; providing controlled substances along with an activity monitor, wherein the controlled substance is provided within a container that includes the activity monitor, the substances being provided in accordance with a valid prescription, wherein the activity monitor records activity events related to dispensing of the controlled substance; the insurer retrieving the recorded activity events; the insurer analyzing the recorded activity events; and the insurer adjusting the premium offered to the individual continued insurance coverage if the analysis of the recorded activity indicates activity that is commensurate with abuse, wherein the container and activity monitor includes a lock-out mechanism and, further comprising the actions of: placing the controlled substance within the container; closing the container and activating the activity monitor in a lock-out state; receiving a lock-out reset request from an insured individual that has received the activity monitored container with the controlled substance; and resetting the lock-out mechanism such that the insured individual can access the controlled substance.

2. The method of claim 1, wherein the action of resetting the lock-out mechanism further comprises receiving a code sequence that is entered by the insured individual to reset the lock-out mechanism.

3. The method of claim 1, wherein activity monitor includes a tone detector and the action of resetting the lock-out mechanism further comprises sending one or more tones over a telephone line to be received by the activity monitor.

4. An activity monitor coupled to a controlled substance container, the activity monitor comprising: a processing unit communicatively coupled to a memory device and integral to the activity monitor; an activity detector communicatively coupled to the processing unit and detecting activity of the container and provide signals to the processing unit related to the detected activity; the processing unit, in response to instructions read from the memory device: receives signals from the activity detector; and records information pertaining to the detected signals into the memory device; and a data access interface that provides access to the recorded information in the memory device to an external device; a signature detector that is accessed by the activity monitor, and wherein the recorded information includes a detected signature proximate to the activity monitor when the activity is detected.

* * * * *